(12) United States Patent
Burns et al.

(10) Patent No.: US 11,564,569 B2
(45) Date of Patent: Jan. 31, 2023

(54) INTRAOCULAR PHYSIOLOGICAL SENSOR

(71) Applicant: GLAUKOS CORPORATION, San Clemente, CA (US)

(72) Inventors: Thomas W. Burns, Dana Point, CA (US); Harold A. Heitzmann, Irvine, CA (US); Kenneth Martin Curry, Oceanside, CA (US); David S. Haffner, Mission Viejo, CA (US); David Applegate, Palm Springs, CA (US); Bruce Nogales, Raleigh, NC (US)

(73) Assignee: GLAUKOS CORPORATION, San Clemente, CA (US)

( * ) Notice: Subject to any disclaimer, the term of this patent is extended or adjusted under 35 U.S.C. 154(b) by 492 days.

(21) Appl. No.: 16/032,945

(22) Filed: Jul. 11, 2018

(65) Prior Publication Data

US 2019/0053704 A1 Feb. 21, 2019

Related U.S. Application Data

(63) Continuation of application No. 13/612,545, filed on Sep. 12, 2012, now Pat. No. 11,363,951.
(Continued)

(51) Int. Cl.
*A61B 3/16* (2006.01)
*A61B 5/00* (2006.01)
(Continued)

(52) U.S. Cl.
CPC ............. *A61B 3/16* (2013.01); *A61B 5/0031* (2013.01); *A61B 5/076* (2013.01); *A61B 5/1112* (2013.01);
(Continued)

(58) Field of Classification Search
CPC . A61B 3/16; A61B 5/0031; A61B 2562/0247; A61B 5/14532; A61B 5/6821; A61B 5/14503; A61B 5/6882
See application file for complete search history.

(56) References Cited

U.S. PATENT DOCUMENTS 3,837,339 A * 9/1974 Aisenberg ............ A61B 5/0002
604/504
7,485,212 B2 2/2009 Willner et al.
(Continued)

FOREIGN PATENT DOCUMENTS

GB 1422172 A 1/1976
GB 2374925 A 10/2002
(Continued)

OTHER PUBLICATIONS

European Office Action for related European Application No. 12769793.6; action dated Jul. 17, 2019; (7 pages).
(Continued)

*Primary Examiner* — Christian Jang
*Assistant Examiner* — Karen E Toth
(74) *Attorney, Agent, or Firm* — K&L Gates LLP

(57) ABSTRACT

An implantable intraocular physiological sensor for measuring intraocular pressure, glucose concentration in the aqueous humor, and other physiological characteristics. The implantable intraocular physiological sensor may be at least partially powered by a fuel cell, such as an electrochemical glucose fuel cell. The implantable intraocular physiological sensor may wirelessly transmit measurements to an external device. In addition, the implantable intraocular physiological sensor may incorporate aqueous drainage and/or drug delivery features.

28 Claims, 18 Drawing Sheets

Related U.S. Application Data

(60) Provisional application No. 61/561,230, filed on Nov. 17, 2011, provisional application No. 61/542,097, filed on Sep. 30, 2011, provisional application No. 61/534,324, filed on Sep. 13, 2011.

(51) Int. Cl.
| | |
|---|---|
| *A61B 5/07* | (2006.01) |
| *A61B 5/11* | (2006.01) |
| *A61B 5/145* | (2006.01) |
| *G16H 10/60* | (2018.01) |
| *G16H 20/10* | (2018.01) |
| *G16H 50/30* | (2018.01) |
| *A61B 5/1473* | (2006.01) |
| *H01M 8/16* | (2006.01) |

(52) U.S. Cl.
CPC ........ *A61B 5/1473* (2013.01); *A61B 5/14503* (2013.01); *A61B 5/14507* (2013.01); *A61B 5/14532* (2013.01); *A61B 5/4836* (2013.01); *A61B 5/4839* (2013.01); *A61B 5/6821* (2013.01); *A61B 5/6867* (2013.01); *A61B 5/6882* (2013.01); *A61B 5/7246* (2013.01); *G16H 10/60* (2018.01); *G16H 20/10* (2018.01); *G16H 50/30* (2018.01); *H01M 8/16* (2013.01); *A61B 2562/0247* (2013.01)

(56) References Cited

U.S. PATENT DOCUMENTS

| | | | | |
|---|---|---|---|---|
| 2002/0049374 A1* | 4/2002 | Abreu | ............... | A61F 9/0017 600/405 |
| 2005/0049578 A1 | 3/2005 | Tu et al. | | |
| 2008/0234598 A1* | 9/2008 | Snyder | ............... | A61B 5/02055 600/545 |
| 2010/0087774 A1* | 4/2010 | Haffner | ............... | A61F 9/00781 604/8 |
| 2010/0137981 A1* | 6/2010 | Silvestrini | ............ | A61M 37/00 623/4.1 |
| 2010/0213057 A1 | 8/2010 | Feldman et al. | | |
| 2010/0249548 A1* | 9/2010 | Muller | ............... | A61B 5/14532 600/318 |
| 2012/0302861 A1* | 11/2012 | Marshall | ............ | A61F 9/00781 600/398 |

FOREIGN PATENT DOCUMENTS

| | | |
|---|---|---|
| WO | 2011/035262 A1 | 3/2011 |
| WO | WO-2012146740 A1 * 11/2012 | ............... A61B 3/16 |

OTHER PUBLICATIONS

Chow, et al.; "Implantable Wireless Telemetry Boards for In Vivo Transocular Transmission"; IEEE Transaction on Microwave Theory and Techniques, vol. 56, No. 12, Dec. 2008; (9 pages).

Chow, et al.; "Wireless Powering and the Study of RF Propagation Through Ocular Tissue for Development of Implantable Sensors"; IEEE Transactions of Antennas and Propagation, vol. 59, No. 6, Jun. 2011; (9 pages).

Gregory Chen, et al; "Circuit Design Advances for Wireless Sensing Applications"; Proceedings of the IEEE, New York; vol. 96, No. 11; Nov. 1, 2010; (20 pages).

Extended European Search Report for related European Application No. 19209752.5; action dated Apr. 15, 2020; (7 pages).

* cited by examiner

INTRAOCULAR PHYSIOLOGICAL SENSOR

RELATED APPLICATIONS

This application is a continuation of U.S. patent application Ser. No. 13/612,545, filed Sep. 12, 2012, and entitled "INTRAOCULAR PHYSIOLOGICAL SENSOR," which claims priority to the following United States provisional patent applications: U.S. Provisional Patent Application No. 61/534,324, filed Sep. 13, 2011, and entitled "INTRAOCULAR PHYSIOLOGICAL SENSOR"; U.S. Provisional Patent Application No. 61/542,097, filed Sep. 30, 2011, and entitled "INTRAOCULAR PHYSIOLOGICAL SENSOR"; and U.S. Provisional Patent Application No. 61/561,230, filed Nov. 17, 2011, and entitled "INTRAOCULAR PHYSIOLOGICAL SENSOR." Each of the foregoing applications is hereby incorporated herein by reference in its entirety to be considered part of this specification

BACKGROUND

Field

The field of the invention generally relates to implantable physiological sensors. In particular, embodiments of the invention generally relate to implantable intraocular sensors for measuring physiological characteristics such as intraocular pressure and glucose concentration.

Description of the Related Art

Some diseases, including glaucoma, diabetes, and others, can be more effectively treated if they are diagnosed early and/or monitored effectively. Glaucoma, for example, is a leading cause of blindness. This disease damages the optic nerve in the eye due to elevated intraocular pressure, which can lead to complete vision loss if untreated. The risk of blindness can be reduced, however, if the elevated intraocular pressure is detected early and appropriately managed. Similarly, diabetes is a serious condition which can be more effectively treated with early-stage detection of elevated blood glucose concentration and more aggressive management with the utilization of, for example, continuous, real-time data.

Accordingly, diagnostic physiological sensors have been developed for implantation within the human body in order to monitor physiological characteristics such as intraocular pressure and glucose concentration. Such implantable sensors may be used to effectively diagnose and treat certain physiological conditions.

SUMMARY

An implantable physiological sensor is disclosed herein. The sensor may include a sensing module that is configured to measure a physiological characteristic of an organism. The physiological sensor may also include a fuel cell that is configured to produce power using a substance found in the organism, and to supply operating power to one or more other components in the physiological sensor.

In some embodiments, the physiological sensor may be configured to be an intraocular sensor that is designed to be implanted within a human eye. The sensing module may be designed to measure, for example, intraocular pressure and glucose concentration in the aqueous humor. In addition, the fuel cell may be an electrochemical fuel cell that generates electrical power using glucose found in the aqueous humor of the eye.

In some embodiments, an implantable intraocular device may comprise: a sensing module configured to measure a physiological characteristic of an organism; a fluid channel; and a fuel cell provided in the fluid channel, the fuel cell being configured to produce power using a substance found in the organism, wherein the fuel cell is configured to supply operating power to one or more components provided in the device. The device may be inserted into a human eye such that the sensing module is provided in the anterior chamber of the eye and such that the fluid channel is in fluid communication with the aqueous humor in the anterior chamber but is at least partially provided in a physiological outflow pathway of the aqueous humor.

BRIEF DESCRIPTION OF THE DRAWINGS

Various embodiments and features of devices, systems, and methods will be described with reference to the following drawings. The drawings, associated descriptions, and specific implementation are provided to illustrate embodiments of the invention and not to limit the scope of the disclosure.

DETAILED DESCRIPTION

There is a need to effectively monitor intraocular pressure within a patient's eye in order to detect, or monitor the progression of, glaucoma. Intraocular pressure can be measured non-invasively using, for example, a tonometer. While tonometers have the advantage of being non-invasive, they have the disadvantages of generally being expensive, non-portable, specialized equipment that requires skilled operation. Accordingly, as a practical matter, it is difficult to use a tonometer to effectively monitor intraocular pressure in a patient's eye with time resolution greater than one measurement every few days or weeks. However, since intraocular pressure can vary significantly over relatively short periods of time, such relatively sparse intraocular pressure measurements may not provide a complete or accurate picture of the patient's risk for glaucoma. It would, therefore, be advantageous to be able to measure intraocular pressure more often or even continuously.

Figure 1A:
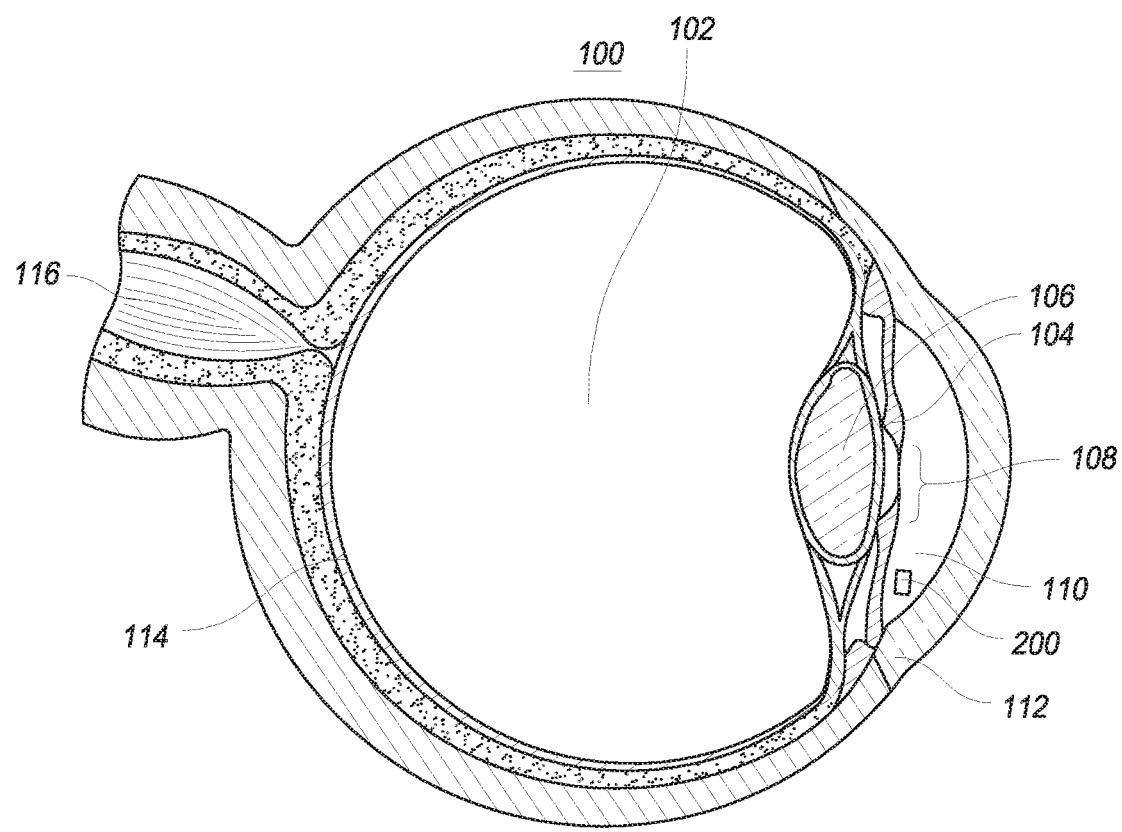
FIG. 1A is a schematic illustration of an implantable intraocular physiological sensor located in a human eye.

FIG. 1A is a schematic illustration of an implantable intraocular physiological sensor 200 located in a human eye 100. For reference, various anatomical features of the eye 100 are labeled in FIG. 1. For example, FIG. 1A shows the vitreous humor 102, the iris 104, the lens 106, the pupil 108, the anterior chamber and aqueous humor 110, the cornea 112, the retina 114, and the optic nerve 116. FIG. 1 also illustrates an intraocular physiological sensor 200 that is located within the anterior chamber of the eye. The intraocular physiological sensor 200 is capable of measuring, for example, intraocular pressure within the eye. The intraocular physiological sensor 200 can also, or alternatively, be designed to measure any of several other physiological characteristics, as discussed herein. It should be understood that the intraocular physiological sensor 200 is not necessarily drawn to scale.

Figure 1B:
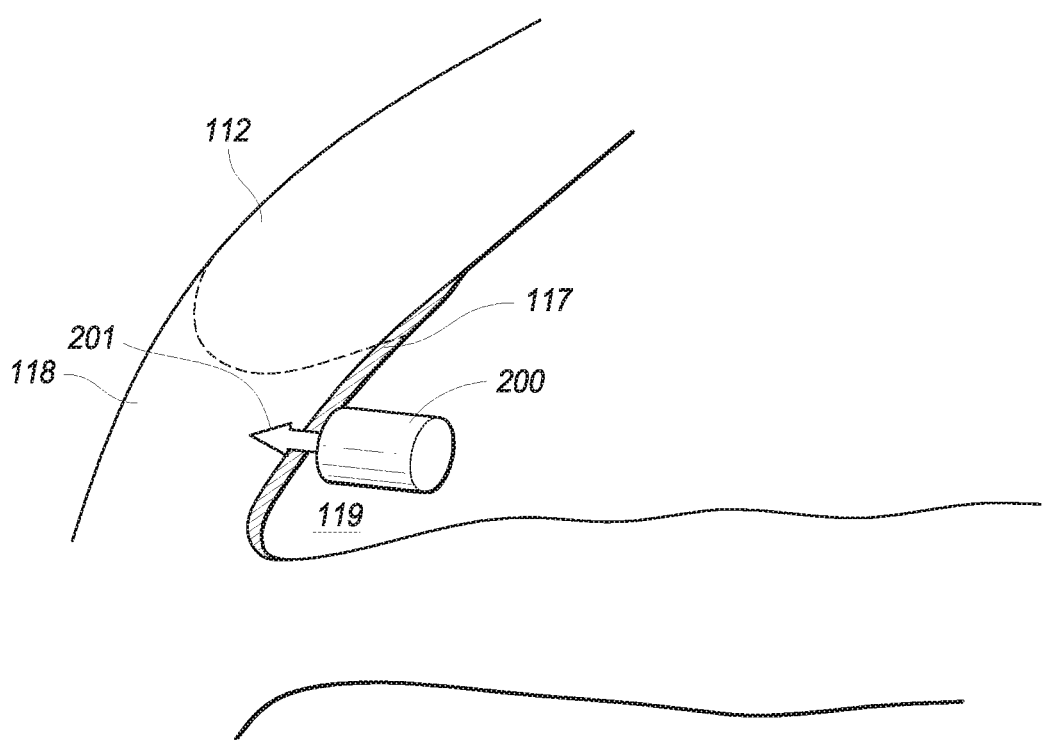
FIG. 1B is a schematic illustration of an implantable intraocular physiological sensor fixed by an anchor through meshwork tissue embedded into scleral tissue in the iridocorneal angle.

In addition, the sensor 200 could be positioned at several different locations within the eye. For example, the intraocular physiological sensor 200 could be fixedly attached or anchored to any suitable anatomical feature of the eye, including but not limited to the sclera or iris, depending upon the particular application. As discussed further below, the intraocular physiological sensor 200 could be fixedly attached or anchored to or within a physiological aqueous humor outflow pathway. The physiological aqueous humor outflow pathways include the "conventional" pathway comprising the trabecular meshwork and Schlemm's canal; and the "uveoscleral" pathway comprising the ciliary body, the sclera, and the supraciliary/suprachoroidal space. FIG. 1B illustrates the location of the sensor 200 fixed by an anchor 201 through meshwork tissue 117 embedded into scleral tissue 118 in the iridocorneal angle 119.

Figure 1C:
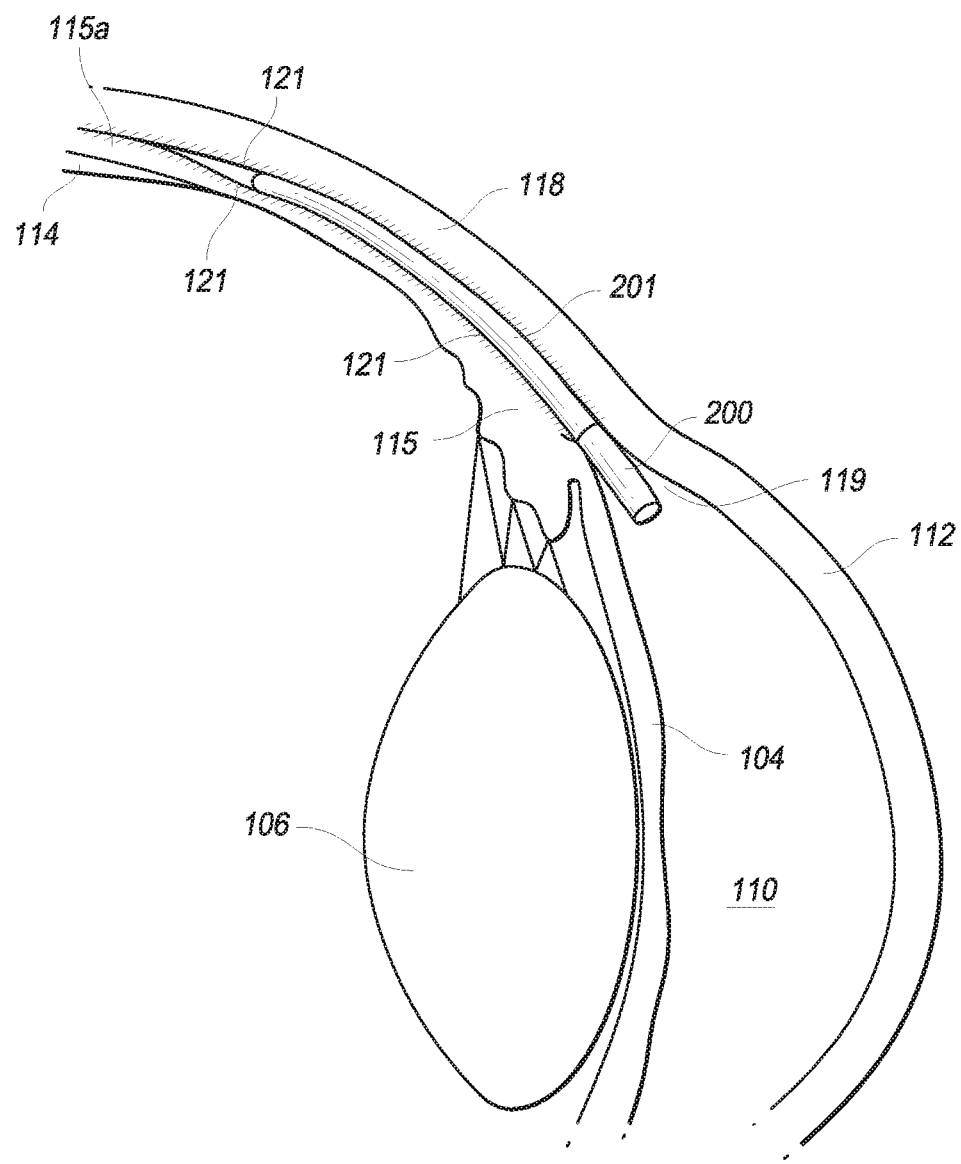
FIG. 1C is a schematic illustration of an implantable intraocular physiological sensor fixed by an anchor within the supraciliary/suprachoroidal space between the ciliary body/choroid and the sclera.

FIG. 1C illustrates the location of the sensor 200 fixed by an anchor 201 within the supraciliary/suprachoroidal space between the ciliary body/choroid and the sclera 118. The ciliary body 115 is contiguous with the choroid 115a. The supraciliary/suprachoroidal space is normally a potential space at the interface between the ciliary body/choroid and sclera. The space may open to accommodate an implant such as the sensor 200 and/or the anchor 201. The supraciliary/suprachoroidal space is thus identified schematically by the hatching 121 in FIG. 1C. FIG. 1C illustrates an example of placement of the intraocular physiological sensor 200 (which may be partially or completely located within the anterior chamber 110; or may be partially or completely located within the supraciliary/suprachoroidal space 121) and the anchor 201. In other embodiments, the physiological sensor that is implanted within the supraciliary/suprachoroidal space could be configured such as the sensor 500 shown in FIG. 5A.

Alternatively, the sensor 200 could be attached to some other ocular implant, such as an intraocular lens. Regardless of location, care should be taken to avoid contact of the sensor with the corneal endothelium.

The intraocular physiological sensor 200 may also, or alternatively, measure glucose concentration in the aqueous humor 110. There is a need to measure glucose concentration within the human body as a means to treat or prevent complications from diabetes. Typically, glucose is measured from the blood or urine. Some implantable glucose sensors have been developed that measure glucose from interstitial fluids. However, the body may have a negative immunological response to such implants, which may degrade the performance of the sensor over time. However, the eye, especially the anterior chamber of the eye, is an immunologically-privileged site within the body. Thus, an implantable sensor for measuring glucose within the eye could have advantages over other implantable sensors that are made to measure glucose in non-immunologically privileged parts of the body. In addition, although the glucose concentration within the aqueous humor may not be identical to blood glucose concentration, the two may be correlated such that a measurement of glucose concentration in the aqueous humor can be predictive of blood glucose concentration.

For some embodiments, such as intraocular pressure sensors, it may be possible to implant the sensor portion completely within the supraciliary/suprachoroidal space. In some embodiments, a modest level of fibrosis may not interfere with satisfactory functioning of the implanted sensor.

As already mentioned, in some embodiments, the intraocular physiological sensor 200 measures both intraocular pressure and glucose concentration in the aqueous humor. This can be advantageous because the glucose concentration measurement can be used to diagnose and/or treat diabetes. Meanwhile, diabetes patients are also at higher risk of developing glaucoma. Thus, there may be a significant overlap of the patient population for whom intraocular pressure and glucose concentration measurements would be valuable.

In some embodiments, the intraocular physiological sensor 200 is wholly or partially powered using a fuel cell that converts a substance found in the human body into, for example, electrical power. For example, in some embodiments, the fuel cell is an electrochemical fuel cell that produces electricity using the glucose dissolved in the aqueous humor. Thus, the glucose itself acts as a renewable fuel for powering the physiological sensor 200.

In contrast, other implantable physiological sensors may be wholly dependent upon batteries or an external source for their power. However, in the case of battery-operated implantable physiological sensors, the capacity of the battery may tend to limit the useful lifetime of such implantable sensors. If the useful lifetime provided by the battery is not adequate for a given application, the implantable sensor may need to be replaced. This is disadvantageous because insertion of an implantable sensor is an invasive process and may require surgery with all of its attendant risks. Alternatively, some implantable physiological sensors rely upon external devices for power (e.g., for real-time operation using the externally-supplied power or to re-charge an internal battery). For example, an implantable physiological sensor may be externally powered via inductive coupling or RF energy from an external device. However, even though such an external power source may remove or reduce the reliance of the implantable physiological sensor's useful lifetime on a battery, external power sources may also introduce other undesirable operating limitations. For example, the time resolution of measurements from such implantable sensors may be limited if measurements can only be performed while the sensor is externally-powered.

Therefore, the fuel cell-operated intraocular physiological sensor 200 is advantageous because it may be expected to have a greater useful lifetime than sensors that are wholly reliant upon a battery or external device for operating power. In addition, such implantable sensors could be used to perform measurements relatively more often, or even continuously.

Figure 2:
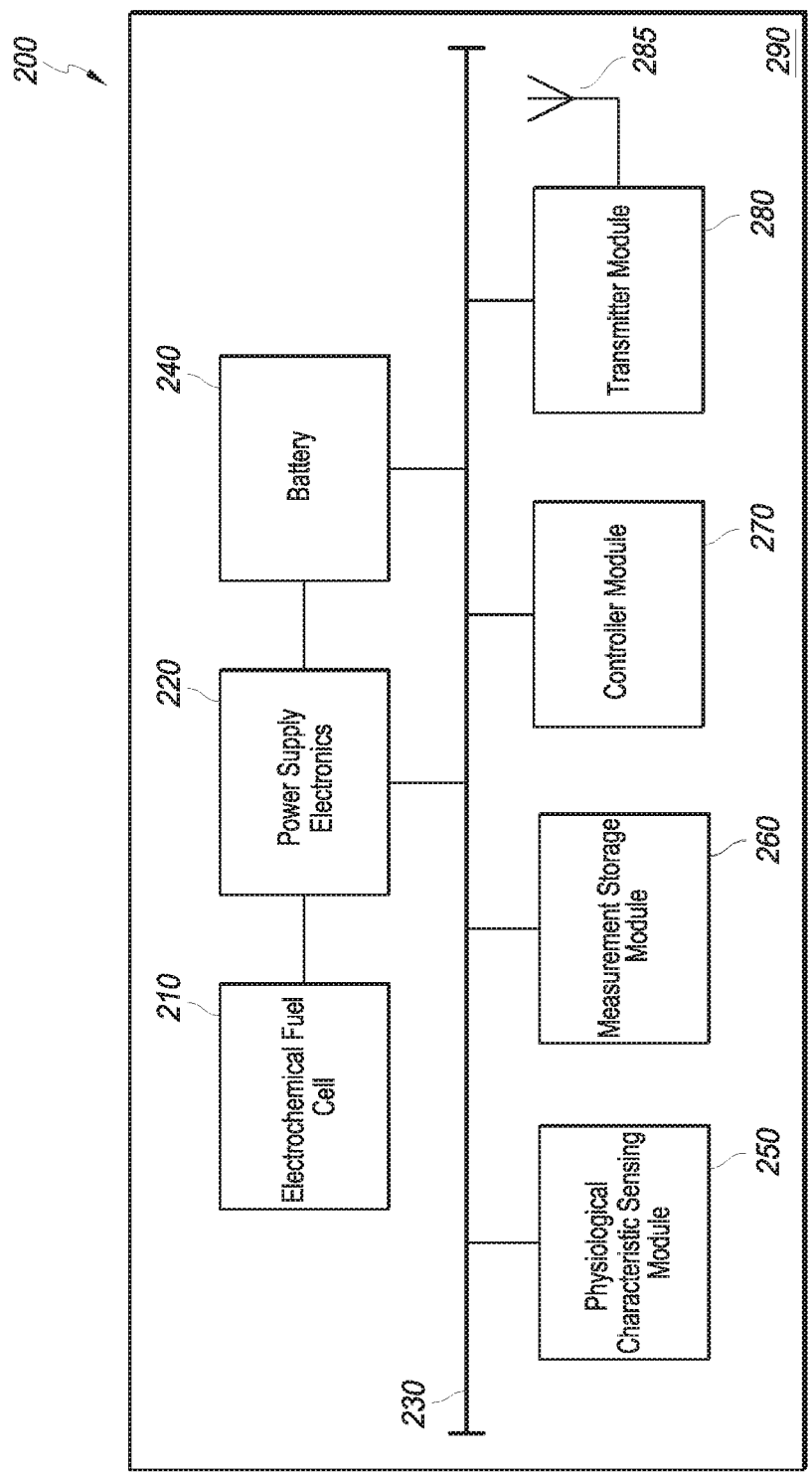
FIG. 2 is a block diagram of an implantable intraocular physiological sensor that includes an electrochemical fuel cell.

FIG. 2 is a block diagram of the implantable intraocular physiological sensor 200. In some embodiments, the implantable intraocular physiological sensor 200 includes an electrochemical fuel cell 210 and power supply electronics 220. The implantable intraocular physiological sensor 200 may also include a battery 240 that is charged by the electrochemical fuel cell 210. In some embodiments, the implantable intraocular physiological sensor 200 includes a physiological characteristic sensing module 250, a measurement storage module 260, a controller module 270, and a transmitter module 280 with an antenna 285. Each of the components of the implantable intraocular physiological sensor 200 may be wholly or partially housed in a biocompatible housing 290. It should be understood that, although the implantable intraocular physiological sensor 200 is described primarily herein with respect to intraocular applications, it may also be used in parts of an organism other than an eye.

In embodiments of the physiological sensor without a fuel cell, there may be an on board power supply such as a battery, or a solar cell combined with a battery or storage capacitor. The battery may be a rechargeable battery that can be recharged by an external device (e.g., a device used to download physiological measurements). In other embodiments of the physiological sensor without a fuel cell, power may be provided by inductive or RF means. In still other embodiments of the physiological sensor without a fuel cell, the sensor may comprise a component of a passive resonant circuit which is interrogated by an external instrument, such as described in "Microfabricated Implantable Parylene-Based Wireless Passive Intraocular Pressure Sensors," by P-J Chen et al., in Journal of Microelectromechanical Systems (2008), volume 17, which is incorporated herein by reference in its entirety.

The physiological characteristic sensing module 250 is a component that performs measurements of a physiological characteristic of interest. For example, the physiological characteristic sensing module 250 outputs a signal (e.g., an electrical signal) that is quantitatively representative of the physiological characteristic under measurement. As discussed herein, the physiological characteristic sensing module 250 may be designed to measure intraocular pressure. There are several different tonometric devices for measuring intraocular pressure. Some sensors are described in U.S. Pat. No. 7,678,065, which is incorporated by reference herein in its entirety. The physiological characteristic sensing module 250 can make use any of these, or future-developed devices. Alternatively, the physiological characteristic sensing module 250 can be designed to measure intraocular glucose concentration. In still other embodiments, the physiological characteristic sensing module 250 can be designed to measure any of the biomarker substances in Table 1, which are listed with the corresponding physiological condition of which they may be indicative.

TABLE 1

| Detected Biomarker | Corresponding Condition |
| --- | --- |
| Interleukin-2, interleukin-6, interleukin-10, interleukin-12, interferon-y, tumor growth factor-β2, tumor necrosis factor-α, macrophage migration inhibitory factor | Uveitis |
| 8-Hydroxy-2'-deoxyguanosine | Age-Related Macular Degeneration (AMD) |
| aB-crystallin, a-enolase, and glial fibrillary acidic protein | AMD |
| Pentosidine, and N-carboxymethyl-lysine | Diabetic Retinopathy |
| Monocyte chemoattractant protein-1 and interleukin-8 | Diabetic Macular Edema (DME) |
| Interphotoreceptor retinoid-binding protein | Blood-Retinal Barrier (BRB) breakdown/ inflammation |
| Survivin | Retinoblastoma/ocular tumor |
| VEGF | Ocular ischemia |
| Amyloid-β | Alzheimer's |
| Intercellular adhesion molecule-1 (ICAM1) | DME |
| TNF-α | Glaucoma |
| TGF-beta3 | Glaucoma |
| Transforming growth factor-beta2 | Glaucoma, diabetes |

In some embodiments, the implantable physiological characteristic sensing module 250 may include a temperature sensor for temperature correction of the physiological sensor 200; and/or may include an oxygen sensor for correcting the physiological sensor 200 for the partial pressure of oxygen.

In some embodiments, the intraocular physiological sensor 200 may comprise a fluorescent sensor, such as disclosed in U.S. Pat. No. 7,653,424 and U.S. Patent Application 2007/0030443, which are incorporated herein by reference in their entirety. In these embodiments, the implanted sensor 200 may not require an onboard power supply, and may be interrogated by an external device.

In some embodiments, the implantable intraocular physiological sensor 200 includes multiple instances of the physiological characteristic sensing module 250. Each instance of the sensing module 250 may be used to measure a different physiological characteristic. As discussed herein, in some embodiments, the physiological sensor 200 includes two sensing modules 250 for measuring intraocular pressure and glucose concentration. Again, the physiological characteristic sensing module(s) 250 can use any known or later-developed device for measuring the foregoing substances, or any other physiological characteristic of interest for a particular application.

In some embodiments, the physiological characteristic sensing module 250 is controlled (e.g., by the controller module 270) to perform a measurement at regular intervals. For example, the sensing module 250 may perform a measurement at least hourly, at least every 15 minutes, at least every minute, or at other intervals, depending upon the particular application. In some embodiments, the physiological characteristic sensing module 250 performs measurements substantially continuously. In this way, trend data regarding the physiological characteristic of interest can be collected so as to provide a more useful or complete picture of how the physiological characteristic changes as a function of time. Alternatively, in some embodiments, readings could be taken less frequently throughout the day (e.g., 4-6 times per day vs. continuously or every 15 minutes) in order to conserve energy (e.g., battery life).

The implantable intraocular physiological sensor 200 may also include a transmitter module 280 that is communicatively coupled to an antenna 285 for wirelessly transmitting measurements from the physiological characteristic sensing module 250 to an external device. In some embodiments, the transmitter module 280 may be replaced by a transceiver module which is capable of also receiving communications (e.g., control commands) from the external device. Any type of suitable transmitter or transceiver device that is known or developed in the future can be used.

In some embodiments, the physiological characteristic sensing module 250 may comprise an electrical circuit that develops a resonant frequency as a function of the level of physiological characteristic, wherein the resonant frequency can be determined with an external device. In this kind of embodiment, the module 250 may employ an antenna for wireless communication, but not necessarily a transmitter (see, for example, Microfabricated Implantable Parylene-Based Wireless Passive Intraocular Pressure Sensors, by P-J Chen et al., in Journal of Microelectromechanical Systems (2008), volume 17, which is incorporated herein by reference in its entirety). In some embodiments, the physiological characteristic sensing module 250 and/or transmitter module 280 may comprise an optical (such as infrared) emitter and/or detector for wirelessly transmitting measurements to, and/or receiving instructions from, an external device.

The transmitter module 280 may be controlled (e.g., by the controller module 270) to transmit measurements at, for example, predetermined intervals, continuously, or upon command from the external device to which the data is being transmitted. In some embodiments, the external device to which measurement data are transmitted may be a data logger that is worn by the patient for storing the measurements until they can be downloaded by a clinician. In other embodiments, the external device may be a handheld reader device used by a clinician to periodically download measurement data that is stored internally by, for example, the measurement storage module 260. The reader device can then transmit the downloaded measurements to a computer (e.g., via the Internet or some other communication network) for processing and/or for analysis by a clinician. In some embodiments, the transmitter module 280 transmits glucose concentration measurements to an insulin pump that is worn by the patient. Such measurements can be used by the insulin pump to control the injection of insulin into the patient's body. The reader device can also provide the downloaded measurements to the patient via a user interface. In the case of glucose concentration measurements, for example, the patient case use the measurements to manage his or her diet and/or exercise.

The implantable intraocular physiological sensor 200 may optionally include a measurement storage module 260. The measurement storage module 260 can be used to internally log measurements from the physiological characteristic sensing module 250, for example, until they can be retrieved by an external device that is communicatively coupled to the measurement storage module 260 via the transmitter module 280. The measurement storage module 260 can be, for example, a solid-state electronic memory device. In some embodiments, the physiological sensor 200 is configured to download, for example, a day or other time period's worth of measurements (e.g., IOP measurements) at a time to an external receiver located, for example, at the bedside of the patient. Data could also be downloaded more or less frequently than daily. In some embodiments, the downloading of data is an automated process. Once measurement data is downloaded to an external device, it can be transferred to a remote reading center for preparation of reports for the patient's ophthalmologist or other managing physician. In addition, the intraocular physiological sensor 200 could include a storage module configured to store other data besides, or in addition to, physiological measurements. For example, the storage module could be loaded with the patient's electronic medical record data, or any other private or sensitive data. In some embodiments, an implantable intraocular device may forgo physiological sensing capabilities and be used primarily to provide a storage module for storing data in a secure but easily accessible, immunologically privileged location. For example, the storage module could hold identification information associated with the patient for security purposes. This information could be accessed, for example, using an external reader to interrogate the implanted device, as discussed herein The implantable intraocular physiological sensor 200 also includes a controller module 270. The controller module 270 can be used, for example, to perform control operations for the other components of the physiological sensor 200. In some embodiments, the controller module 270 may provide commands to the physiological characteristic sensing module 250 to perform measurements. The controller module 270 may also control the writing and reading of data to the measurement storage module 260 and the operation of the transmitter module 280. In addition, the controller module 270 may control power settings of the electrochemical fuel cell 210, the power supply electronics 220, and battery 240. As discussed further below, the interconnecting lines shown in FIG. 1 primarily represent power supply connections. It should be understood, however, that signal and/or command lines can be provided between any and all of the components of the sensor 200 (e.g., between the controller module 270, the physiological characteristic sensing module 250, the measurement storage module 260, the transmitter module 280, and/or the power supply electronics 220, etc.) as necessary.

The controller module 270 may also perform other functions. For example, in some embodiments, the controller module 270 can perform data processing tasks on the measurements collected by the physiological characteristic sensing module 250, though in other embodiments any such required data processing can be performed by an external device after downloading the measurements in order to avoid the power demands of such onboard processing. In addition, the controller module 270 may monitor the collected measurements and output alarm signals (e.g., to an external device via the transmitter module 280) if the physiological characteristic that is being monitored reaches some threshold value or if immediate notification is otherwise considered necessary. For example, an alarm signal can be triggered if the sensor detects a potentially dangerous low blood sugar level. The controller module 270 can also perform measurement data compression (to allow for more measurements to be stored on the measurement storage module 260). In addition, the controller module 270 can issue commands to other components of the physiological sensor 200 (e.g., the transmitter module 480, the measurement storage module 460, the physiological characteristic sensing module 450, etc.) to shut down or enter a power-saving state when not in use.

As briefly discussed above, the implantable intraocular physiological sensor 200 may include a fuel cell such as the electrochemical fuel cell 210. In some embodiments, the electrochemical fuel cell 210 uses glucose in the aqueous humor 108 to produce electrical power from a chemical reaction with the glucose. The electrical power produced by the electrochemical fuel cell 210 can be used to satisfy the power demands, whether in whole or in part, of any or all of the other components of the implantable intraocular physiological sensor 200. An electrical bus 230 is illustrated in FIG. 2. The electrical bus 230 is energized by the electrochemical fuel cell 210 (e.g., via power supply electronics 220 and/or a battery 240). Any other components of the implantable intraocular physiological sensor 200 can be connected to the electrical bus 230 (as illustrated by the interconnecting lines in FIG. 2) to receive operating power, as necessary.

The electrochemical fuel cell 210 can be connected to power supply electronics 220. The power supply electronics 220 can include, for example, a voltage regulator, a voltage converter, or any other electrical component that may be desirable for conditioning the electrical power output by the electrochemical fuel cell 210 so that it can be satisfactorily used by other electrical components within the implantable intraocular physiological sensor 200. In some embodiments, the electrochemical fuel cell 210 can be used to charge a battery 240. A battery 240 may be useful, for example, in cases where data transmission from the transmitter module 280 requires a burst of power that is greater than the instantaneous power available from the electrochemical fuel cell 210. The battery 240 may also be useful in providing a steady level of electrical power to other components of the implantable intraocular physiological sensor 200 in circumstances where, for example, the supply of fuel (e.g., glucose) used by the fuel cell 210 is irregular. Although the implantable intraocular physiological sensor 200 includes the electrochemical fuel cell 210 to at least partially satisfy power demands, it should be understood that the presence of the fuel cell 210 does not necessarily preclude the use of other internal or external power sources to provide additional operating power to the physiological sensor 200. Moreover, in some embodiments, the intraocular physiological sensor 200 may include two or more batteries in addition to, or in place of a fuel cell. In such embodiments, one battery can become active after another becomes too discharged for further use, thus extending the useful life of the sensor. The changeover between batteries can be controlled, for example, by software and/or hardware.

According to some estimates, the average power consumption of the physiological sensor 200 may be less than about 10 nW, assuming that a measurement is made by the physiological characteristic sensing module 450 every 15 minutes and that the transmitter module 480 performs data transmission once daily. Thus, in some embodiments, the electrochemical fuel cell 210 has an average power output of at least about 10 nW. However, if, for example, measurements or data transmission are performed more frequently, or if more than one physiological characteristic is monitored, etc., then power demands may be greater. Therefore, in some embodiments, the electrochemical fuel cell 210 produces an average power output of at least about 10 µW, or more.

The implantable intraocular physiological sensor 200 may also include other modules in addition to those that are specifically illustrated. For example, the implantable intraocular physiological sensor 200 could include a Global Positioning System (GPS) module for providing location information about the patient's whereabouts. The GPS module could, for example, store a reading of the patient's location at each time that a physiological measurement is performed. The location information could be downloaded from the physiological sensor 200 along with physiological measurements and used, for example, to access a weather database with barometric pressure information from the patient's location. Such barometric pressure information can then be used to perform any necessary corrections to the intraocular pressure measurements that were detected by the physiological sensor 200.

Figure 3:
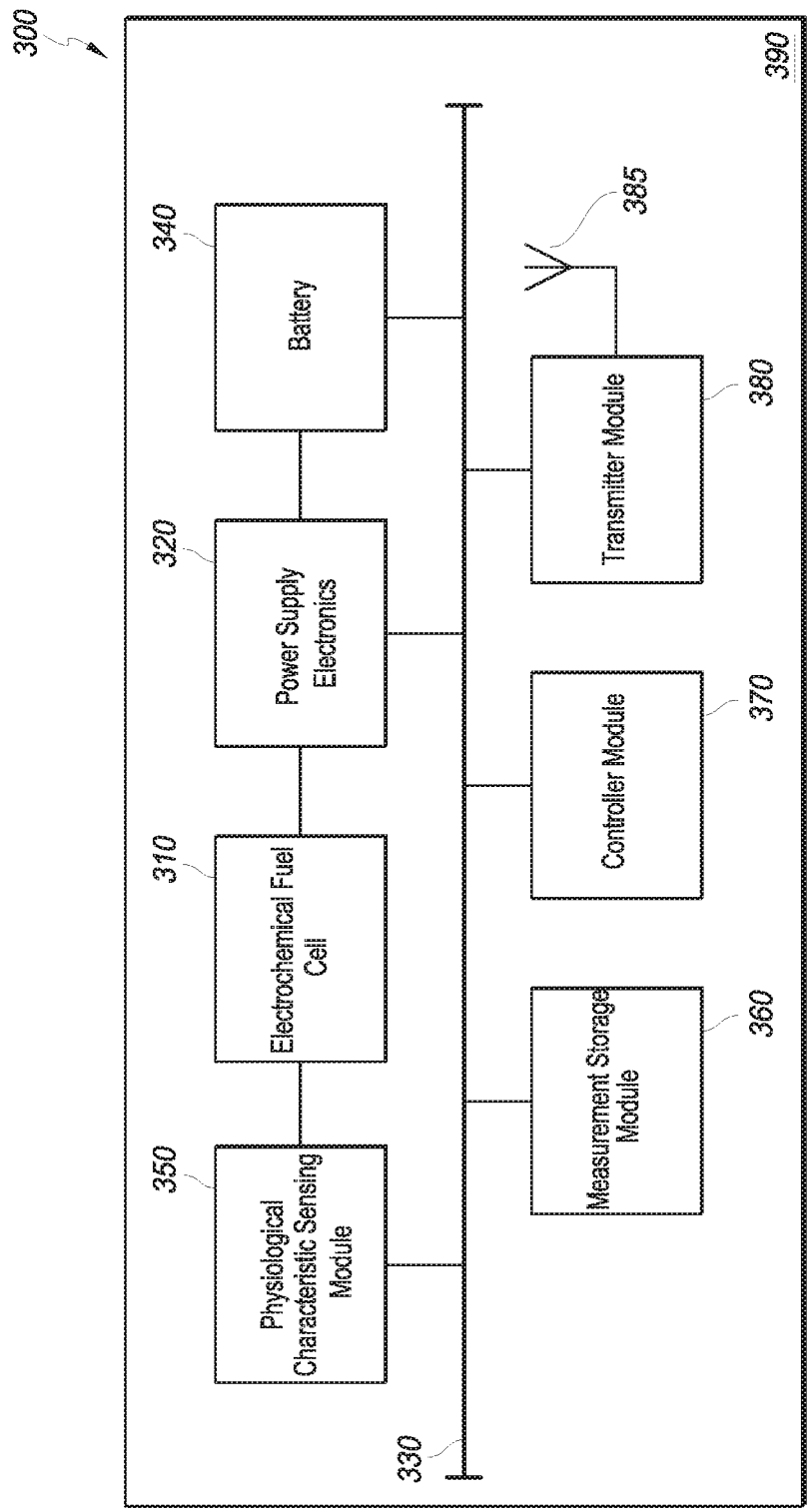
FIG. 3 is a block diagram of an implantable intraocular physiological sensor in which a physiological characteristic is measured based on the output from an electrochemical fuel cell.

FIG. 3 is a block diagram of an implantable intraocular physiological sensor 300 in which a physiological characteristic is measured based on the output from an electrochemical fuel cell 310. The implantable intraocular physiological sensor 300 can include, for example, an electrochemical fuel cell 310, power supply electronics 320, an electrical bus 330, a battery 340, a physiological characteristic sensing module 350, a measurement storage module 360, a controller module 370, a transmitter module 380 coupled to an antenna 385, and a biocompatible housing 390. Each of these components can be similar to the corresponding components described with respect to FIG. 2.

In the implantable intraocular physiological sensor 300, the physiological characteristic sensing module 350 measures the amount of the substance (e.g., in the vicinity of the physiological sensor 300) that is used by the electrochemical fuel cell 310 to generate power. For example, the electrochemical fuel cell 310 may be a glucose fuel cell and the sensing module 350 may be designed to measure glucose concentration in the aqueous humor. In this embodiment, the sensing module 350 is shown with a direct connection to the electrochemical fuel cell 310 to indicate that the sensing module 350 measures glucose concentration based upon the electrical current or voltage that is output by the electrochemical fuel cell 310. For example, when glucose is present in the aqueous humor of the eye in greater concentrations, the electrochemical fuel cell 310 may produce a larger electrical current or voltage, and vice versa for smaller glucose concentrations. The glucose measurement provided by the physiological characteristic sensing module 350 may be, for example, proportional to the electrical current or voltage from the fuel cell 310.

Figure 4:
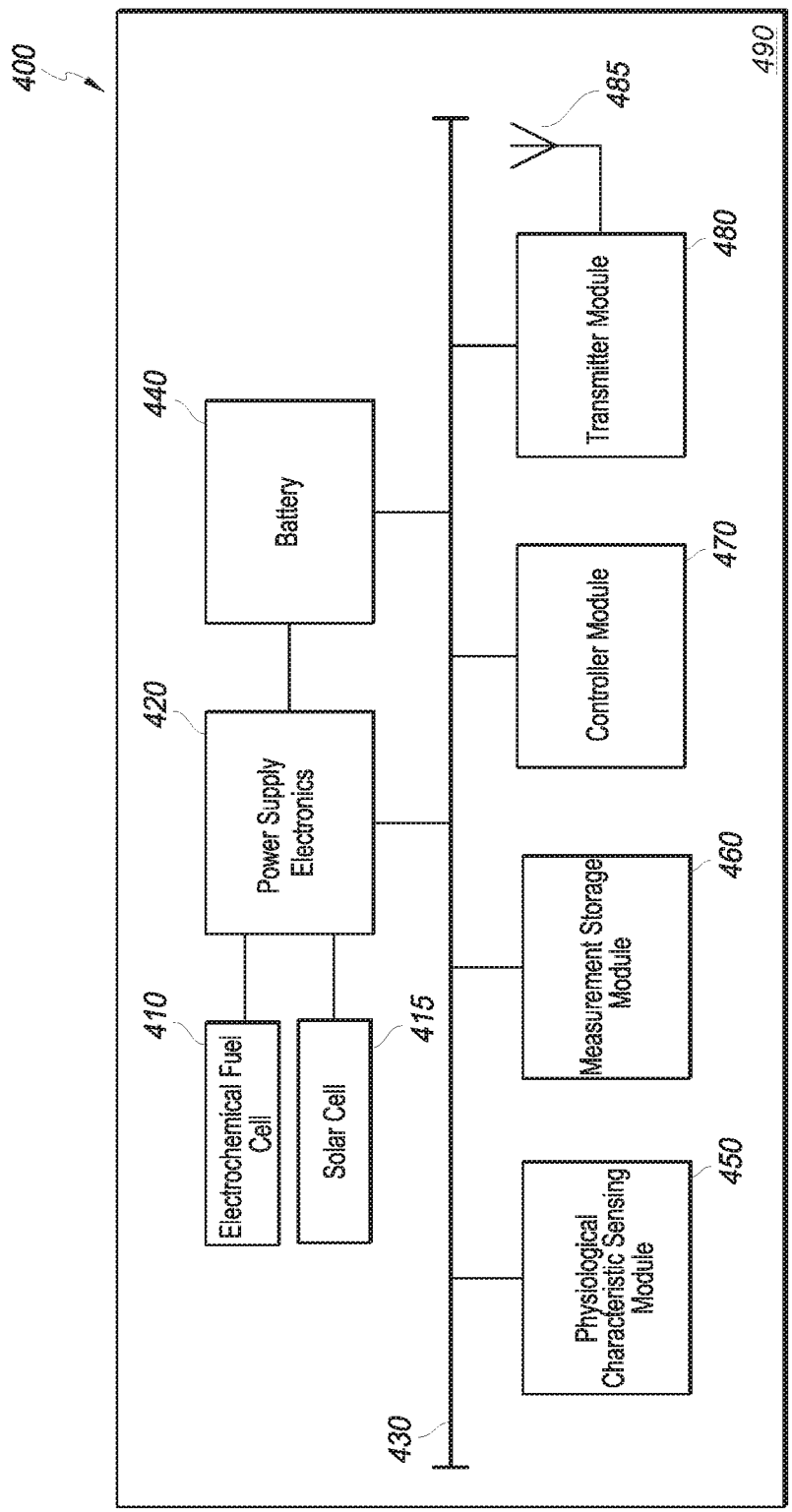
FIG. 4 is a block diagram of an implantable intraocular physiological sensor that includes an electrochemical fuel cell and/or a solar cell.

FIG. 4 is a block diagram of an implantable intraocular physiological sensor 400 that includes an electrochemical fuel cell 410 and/or a solar cell 415. The electrochemical fuel cell 410, power supply electronics 420, electrical bus 430, battery 440, physiological characteristic sensing module 450, measurement storage module 460, controller module 470, transmitter module 480 and antenna 485, and biocompatible housing 490 can be similar to the corresponding components described with respect to FIGS. 2 and 3.

The implantable intraocular physiological sensor 400 can also include a solar cell 415. The solar cell 415 generates power from any light that enters the eye 100. The solar cell 415, which can be of any suitable type currently known or developed in the future, can be used to at least partially satisfy power demands of the various components of the physiological sensor 400. For example, if the electrochemical fuel cell 410 is unable to satisfy the power requirements of the physiological sensor 400, then the solar cell 415 can be used as an additional power source to help satisfy those requirements. In some embodiments, the solar cell 415 is used to energize an electrical bus 430 (e.g., via the power supply electronics 420) to which other components of the physiological sensor 400 are connected. The solar cell 415 can also be used to charge a battery 440 so that the physiological sensor 400 can still operate in dark conditions. The solar cell 415 can be included, for example, in addition to, or in place of, the electrochemical fuel cell 410.

As discussed above, the foregoing embodiments may be used in the diagnosis or treatment of glaucoma. About two percent of people in the United States have glaucoma. Glaucoma is a group of eye diseases that causes pathological changes in the optic disk and corresponding visual field loss, resulting in blindness if untreated. Intraocular pressure elevation is a major etiologic factor in glaucoma. In certain embodiments, a sensor implant, such as those described herein, may be used and/or delivered together with one or more implants that provide for drug delivery to the eye and/or drainage of aqueous humor from the anterior chamber as a treatment for glaucoma.

In glaucomas associated with an elevation in intraocular pressure ("IOP"), the source of resistance to outflow of aqueous humor is mainly in the trabecular meshwork. The tissue of the trabecular meshwork allows the aqueous humor, or aqueous, to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is an essentially constant flow of aqueous humor from the ciliary body to the eye's anterior chamber. The anterior chamber pressure is determined by a balance between the production of aqueous and its exit through the trabecular meshwork (major route) or uveoscleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Two primary methods of alleviating the imbalance between the production and drainage of aqueous humor are use of pharmaceuticals that reduce IOP and use of ocular implants that enhance drainage of aqueous from the anterior chamber. Implants may provide a route to allow drainage of aqueous from the anterior chamber. The implant may be designed to allow drainage to any suitable location, including the subconjunctival space (including use of a bleb) and a physiologic outflow path such as Schlemm's canal or the uveoscleral outflow pathway (including suprachoroidal space and/or supraciliary space).

Any of a wide variety of ocular implants to enhance aqueous drainage may be used in connection with other implants as disclosed herein. For example, U.S. Pat. Nos. 6,638,239 and 6,736,791 disclose devices and methods of placing a drainage device or shunt ab interno. The stent includes a hollow, elongate tubular element, having an inlet section and an outlet section. The outlet section may optionally include two segments or elements, adapted to be positioned and stabilized inside Schlemm's canal. In one embodiment, the device appears as a "T" shaped device. In another embodiment, the device appears as a "L" shaped device. In still another embodiment, the device appears as a "I" shaped embodiment. The entire contents of each one of these patents are hereby incorporated by reference herein.

Other implants are suitable for use in providing aqueous drainage. For example, one embodiment of a drainage implant has a longitudinal axis and comprises a first portion sized and configured to reside at least partially in the anterior chamber and a second portion sized and configured to reside within Schlemm's canal, the suprachoroidal space, or another physiological outflow pathway of the major or minor route. The first portion also includes an inlet section that communicates with a lumen that runs along the longitudinal implant axis and communicates with one or more exit or outflow ports in the second portion of the device. Another type of device may be in a form that resembles a rivet, wherein there is an inlet portion that resides in the anterior chamber, a distal portion having one or more outlets and is adapted to reside in a physiologic outflow pathway (e.g. Schlemm's canal, uveoscleral outflow pathway, suprachoroidal space, supraciliary space), and an intermediate portion adapted to extend through tissue and provide fluid communication between the inlet and distal portions. The devices may also comprise one or more retention features (e.g. ridges, barbs, protrusions, etc.) to assist in retaining the device in the desired location in the eye. Such devices may also include one or more drugs. These and other suitable implants are disclosed in U.S. Pat. Nos. 7,135,009, 7,857, 782, 7,431,710, and 7,879,001, the disclosures of which are hereby incorporated by reference in their entireties.

Any of the foregoing implants may feature a drug coating in addition to providing drainage, wherein the drug may be any type as disclosed herein, including drugs to treat glaucoma or other eye conditions, and drugs to prevent or reduce scarring, fibrosis, clotting and other deleterious effects that may result from implantation of a device. In other embodiments, the devices may be adapted to deliver one or more drugs over a desired period of time by providing the drug in bulk form, e.g. placed in a recess or lumen in the device, or in the form of a tablet or mass that is affixed to or contained within the body of the device. Bulk drug may also take the form of a tiny pellet or tablet which may be placed in a recess or lumen of a device or affixed to the device. Where the drug is present in bulk form, the device may also include a drainage lumen. In some embodiments, the drainage lumen also includes drug so that drainage of aqueous facilitates drug elution. Devices may also include both bulk drug and a drug coating. Examples of such devices are found in International Patent Application Publication No. WO 2010/135369, the disclosure of which is hereby incorporated by reference in its entirety.

Figure 5A:
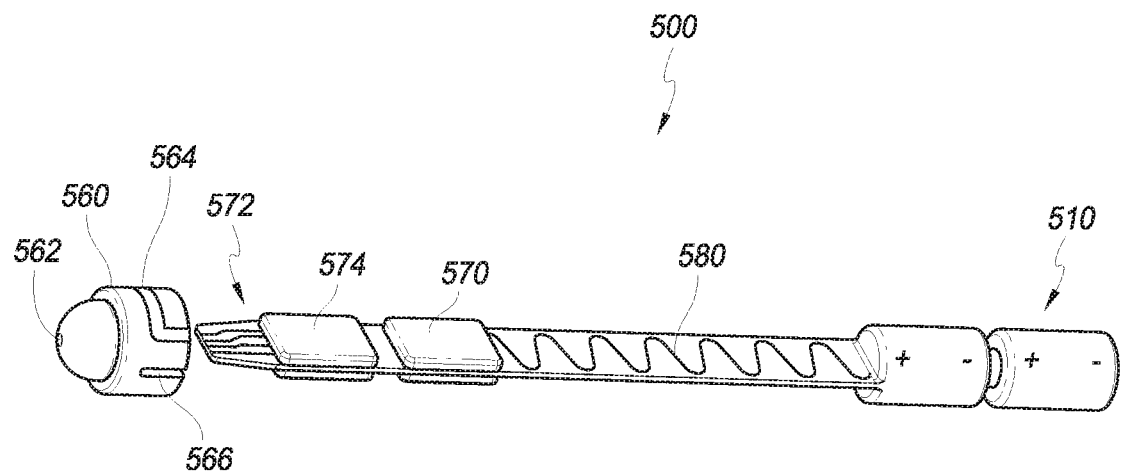
FIG. 5A is a schematic illustration of an implantable intraocular physiological sensor that also enhances drainage of the aqueous humor to help treat glaucoma.
Figure 5B:
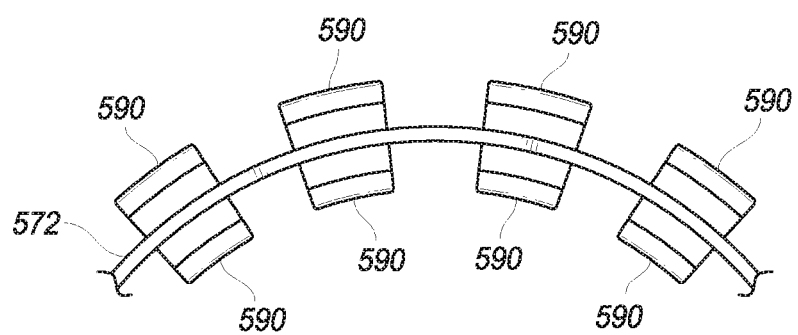
FIG. 5B is a schematic illustration of a circuit carrier member that can be used in the device of FIG. 5A.

FIG. 5A is a schematic illustration of an implantable intraocular physiological sensor 500 that also enhances drainage of the aqueous humor to help treat glaucoma. The physiological sensor 500 includes a physiological characteristic sensing module 560, which could be, for example, electromechanical (such as a capacitive intraocular pressure sensor), electrochemical (such as an amperometric glucose sensor), or optical (such as a fluorescent glucose sensor). The physiological sensor 500 also includes electrochemical fuel cells 510 and various electronic components, such as those described herein. The implantable device can also incorporate onboard memory, logical control (such as microprocessor), software, firmware, digitization, and wireless (radiofrequency or optical) communication. For example, the sensor 500 can include a controller module 570, a signal conditioning and analog-to-digital conversion module 574, a transmitter, etc. The transmitter can include an antenna 580. Some or all of these components can be provided on, or attached to, a carrier member 572. In some embodiments, the carrier member 572 is a circuit board. As discussed further herein, the sensor device 500 may be designed so as to be implantable at or in various anatomical features of the eye. Accordingly, in some embodiments, the carrier member 572 is flexible so as to allow it to satisfactorily conform to a desired anatomical feature. The flexible carrier member 572 can be, for example, a bendable film, such as Kapton™ (polyimide), or comprise a flexible electrical circuit, known as a "flex circuit." FIG. 5B is a schematic illustration of an embodiment of the carrier member 572. As illustrated, the carrier member 572 can be made from a flexible material that allows the carrier member 572 to be deformed into a curvilinear form. Various modules 590 can be mounted on the carrier member 572 at spaced apart intervals on both sides of the carrier member. The modules 590 can also be stacked. The illustrated modules 590 can represent, for example, any of the modules discussed herein (e.g., controller, transmitter, etc.). Signal connection lines such as electrical traces can be formed on the carrier member 572 between the various modules 590. Since the modules 590 are mounted on the carrier member 572 at spaced apart intervals, the combination of the carrier member 572 and the modules 590 can more freely the form to take the shape of the anatomy where it may be implanted.

Although not illustrated, the fuel cells 510 and the carrier member 572, as well as its mounted electronic components, are provided within a fluid channel. The fluid channel can be, for example, a lumen or sheath that is generally cylindrical in shape, though other shapes are possible as well. In some embodiments, the lumen or sheath may have a generally circular, square, or rectangular cross-sectional shape. Square and rectangular cross-sectional shapes may be advantageous in terms of more efficiently being able to fit circuit boards, electronics, etc. within the sheath. Although the sheath may have a generally square or rectangular cross-sectional shape, the corners of the square or rectangular may be rounded in order to ease insertion of the device into, for example, Schlemm's canal or the suprachoroidal space and avoid any damage to the tissue. The fluid channel can have an inlet port that is designed to be in fluid communication with the aqueous humor in the eye when the sensor device is implanted at the intended surgical location. The fluid channel can also have a fluid outlet port that is designed to be in communication with a physiological outflow pathway of the aqueous humor. For example, the outlet port of the fluid channel could be located in the suprachoroidal space or in Schlemm's canal. As the aqueous humor flows through the fluid channel, it can come into contact with the fuel cells 510, thus providing fuel (e.g., glucose dissolved in the aqueous humor) to the fuel cells for the generation of electrical power to operate the sensor device 500. In addition, the sensor device 500 may include a pumping module (not shown) to assist the flow of aqueous through the fluid channel.

In some embodiments, the physiological characteristic sensing module 560 is designed to measure intraocular pressure. Accordingly, in such embodiments, the sensing module 560 may be designed to be located in the anterior chamber of the eye when the device 500 is implanted at the intended destination in the eye. However, as discussed herein, the sensing module 560 may also, or alternatively, be designed to measure other physiological characteristics. As illustrated in FIG. 5A, the sensing module 560 may be a modular component that is detachable from the remainder of the device 500. In the particular illustrated embodiment, the sensing module 560 includes a notched connector 566 that mates with the carrier member 572, which is illustrated as a circuit board. The circuit board also includes electrical lines for communicating signals and power to/from the sensing module 560. The sensing module 560 may also include a connector 564 that mates with the fluid channel, which encloses the carrier member 572, electronic components (e.g., 570, 574, 580) and the fuel cells 510. In particular, the sensing module 560 may be a cap that mounts in one open and of a sheath that serves as the fluid channel. A fluid inlet port 562 can be provided in the sensing module 560 to allow the fluid channel to be in fluid communication with the aqueous humor that surrounds the sensing module.

As discussed herein, the fuel cells 510 can be glucose fuel cells. While two separate fuel cells are illustrated in FIG. 5A, other embodiments may use only one, or some other number, of fuel cells. Glucose-containing aqueous humor can enter the inlet port 562 of the sensing module 560. The aqueous humor can then flow through the fluid channel that is capped by the sensing module, over and around the carrier member 572 and electrical components (e.g., controller module 570, signal conditioning module 574, antenna 580), and then over and around the fuel cells 510 before exiting an outlet port of the fluid channel into a physiological outflow pathway of the aqueous humor.

Based on initial estimates, the glucose fuel cells 510 may be capable of providing approximately 1.5 mW/cm$^2$ of surface area. The size and surface area of the fuel cells 510 may vary from application to application depending upon available space. However, an initial estimate for an application where the sensor device 500 is sized to be insertable into the suprachoroidal space is that each of the fuel cells may have a surface area of about $2.9 \times 10^{-3}$ cm$^2$. Based on these estimates, each of the fuel cells 510 may produce about $4.3 \times 10^{-3}$ mW. Thus, the combination of the two fuel cells would provide approximately 8 µW. According to initial estimates, the glucose fuel cells 510 would require approximately $4.8 \times 10^{-8}$ moles of glucose per minute in order to generate the 8 µW of power. Based on typical aqueous humor production rates and glucose concentrations in the aqueous, the glucose required by the fuel cells may be a small percentage of the available glucose in the eye (e.g., 0.4%).

In some embodiments, the sensor device 500 is estimated to consume on the order of the few microwatts while performing a measurement and a few picowatts while in a standby low-power mode between measurements. Transmission of the measurements to an external device may require more power, however; perhaps on the order of milliwatts for a short period of time. The precise power demands of the sensor device 500 will depend on numerous factors, including the frequency of measurements, the frequency and required range of data transmission to an external device, etc. However, additional, or fewer, fuel cells can be used depending upon the power requirements of the sensor device 500.

Figure 6:
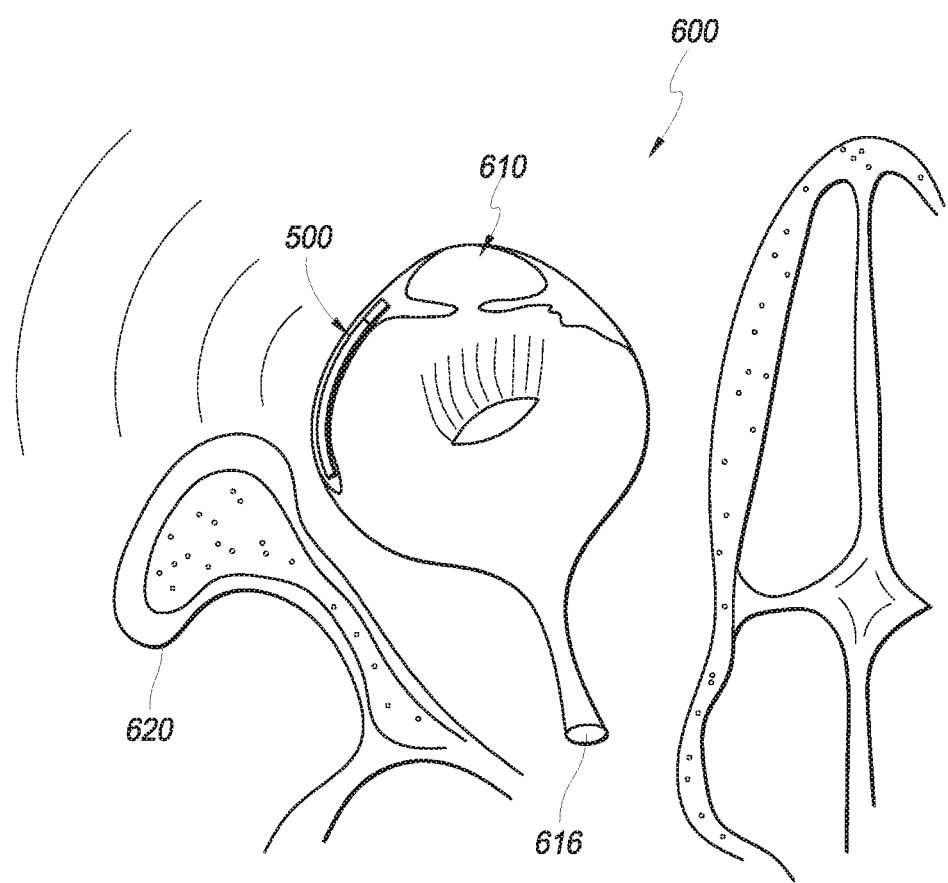
FIG. 6 is a schematic illustration showing the device of FIG. 5A implanted in the eye.

FIG. 6 is a schematic illustration showing the device 500 of FIG. 5A implanted in the eye 600. In particular, FIG. 6 is a superior view of the placement of the sensor device 500, which also shows transmission of electromagnetic waves from the antenna 580. FIG. 6 shows the eye 600, with the anterior chamber 610, the optic nerve 616, and various other anatomical features. The cheekbone 620 is also shown.

In some embodiments, the sensor device 500 is designed to be implanted and/or anchored at least partially in the suprachoroidal space of the eye, as illustrated. In such embodiments, the sensor device 500 may be designed with a generally elongate, cylindrical shape having an outer diameter or dimension of about 0.6 mm or less. In some embodiments, the generally elongate, cylindrical sensor device 500 measures about 3-14 mm in length. In some embodiments, the generally elongate, cylindrical sensor device 500 is about 4 mm in length, has an outer diameter or dimension of about 360 µm and inner diameter or dimension of about 160 µm. The body of the sensor device 500 can be made of various materials, including polyethersulfone (PES). In addition, in some embodiments, the sensor device can be inserted into the anterior chamber via a self-sealing incision at or near the limbus, although it could also be inserted through other openings such as the incision made for cataract surgery, trabeculectomy or other ophthalmic surgical procedures. As already discussed, the sensor device 500 may be inserted such that the sensing module 560 remains in the anterior chamber 610 and in fluid communication with the aqueous humor, while the remaining portion of the device 500 is at least partially located in the suprachoroidal space and/or other portion of the uveoscleral outflow pathway. This placement allows the sensing module 560 to measure intraocular pressure within the anterior chamber 610, while also providing for aqueous drainage through the fluid channel to the suprachoroidal space. In some embodiments, certain components of the sensor device 500, including but not limited to a pressure sensor module and solar cell, could be designed to be insertable into the anterior chamber through a tiny incision as part of a device which would anchor in the suprachoroidal space and subsequently unfurl or enlarge once in position or during positioning. In embodiments with this unfurling or enlarging action, rigid componentry could be mounted to a flexible backer. Other intraocular placements for the sensor device 500 may also be used. For example, the sensor device 500 may be designed to be at least partially inserted into Schlemm's canal. In such embodiments, the sensor device 500 may have, for example, a generally elongate, cylindrical shape with a diameter or dimension of about 150 µm or less. As already discussed, in some embodiments (such as intraocular pressure sensors), the sensor device 500 may be implanted completely within the suprachoroidal space of the eye.

The sensor device 500 may be configured for placement in the supraciliary or suprachoroidal space by making it elongated in one dimension, and narrow or thin in a second and/or third dimension. The elongated dimension may be in the range of 2-25 mm, or more specifically 3-14 mm, while the narrow dimension(s) may be less than 1 mm, and preferably less than 0.6 mm in order to (a) facilitate insertion into the eye through a small gauge insertion needle or cannula; and/or (b) make the device flexible enough to conform to curvature of the anatomy (for example, the curvature of the sclera).

At least one possible advantage of the placement illustrated in FIG. 6 is that the antenna 580 may be largely unobscured by bone, such as the orbital bone or cheekbone 620. Thus, the antenna 580 may only be required to transmit through soft tissue. This can ease the power demands of the transmitter and/or increase the transmission range of the device.

Another advantage of placement of the sensor device 500 in the anterior chamber is that this body location is immunologically privileged, as discussed herein. In other body locations, collagen ("fibrous") encapsulation may occur as a reaction to the presence of a foreign body. Fibrous encapsulation is an obstacle that may reduce the useful life of implanted biomedical sensors. The anterior chamber, in contrast, is one of a very few sites in the body demonstrating "immune privilege" such that a foreign body may be introduced without eliciting an inflammatory immune response. Therefore, a foreign body such as a glucose (or other) biosensor, implanted with minimum trauma and located at least in part within the anterior chamber, may well experience less fibrous encapsulation and a longer useful life than the same biosensor implanted elsewhere in the body.

As discussed herein, the sensor device 500 can be used as part of a system whereby intraocular pressure values measured and temporarily stored by the implanted sensor are read automatically by a monitor, such as a device at a patient's bedside that interrogates the implanted sensor during sleep. In some embodiments, the bedside monitor would interface to, for example, the internet, and automatically send data to a doctor's office for evaluation. This system could include time stamping and temporary storage in memory of intraocular pressure measurements made by the implanted sensor. The sensor measurements could be continuous or intermittent, and the device could be switchable, between active and quiescent states.

Figure 7:
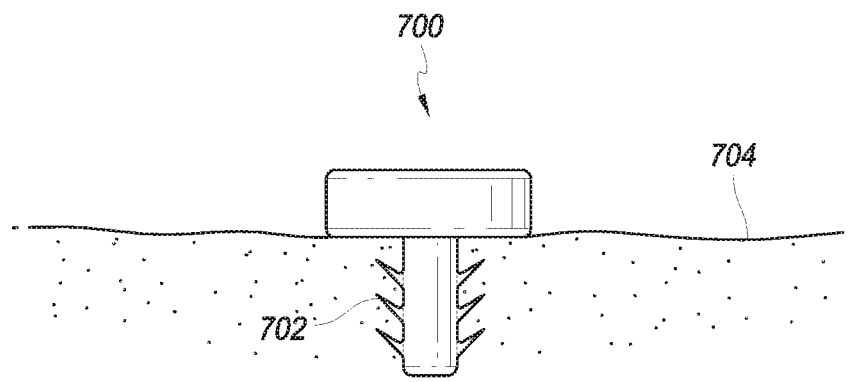
FIG. 7 is a schematic illustration of an implantable intraocular physiological sensor with an anchoring member.

FIG. 7 is a schematic illustration of an implantable intraocular physiological sensor 700 with an anchoring member 702. The anchoring member 702 can be used to fixedly attach the sensor 700 to eye tissue 704, such as eye tissue comprising a physiological outflow pathway for aqueous humor. The anchoring member 702 is illustrated with barbed retention features, but it can include any of many different types of retention features. In addition, the physiological sensors 700 can include any of the features discussed herein with respect to any other sensor device.

Figure 8:
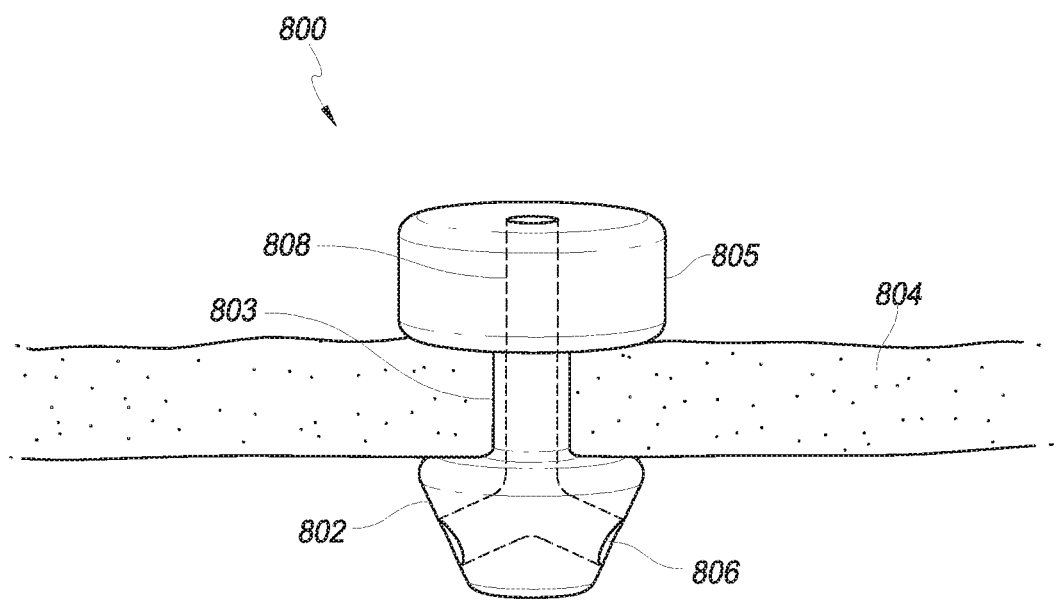
FIG. 8 is a schematic illustration of an implantable intraocular physiological sensor with an anchoring member and a fluid channel.

FIG. 8 is a schematic illustration of an implantable intraocular physiological sensor 800 with an anchoring member 802 and a fluid channel. Thus, the physiological sensor 800 advantageously combines aqueous drainage features with physiological characteristic sensing features. The sensor 800 includes a head portion 805 in which a sensing module, a controller module, a transmitter, a fuel cell, etc. can be included, as discussed herein. The head portion 805 can be attached to the anchoring member 802 by a stem portion 803. In some embodiments, the anchoring member 802 is a tapered bulbous portion that allows penetration into the eye tissue 804, and retention in such eye tissue. In some embodiments, the length of the stem portion 803 corresponds to the thickness of the eye tissue 804 where the sensor device 800 is designed to be located.

The sensor device 800 can also include a fluid channel 808, which is illustrated by dotted lines to indicate that it is an interior feature. In some embodiments, the fluid channel 808 has an inlet port at the head portion 805 of the sensor device 800. The fluid channel 808 can extend from the head portion, which is designed to be in fluid communication with the aqueous humor when the sensor device 800 is implanted, through the stem portion 803, to the anchoring member 802. In some embodiments, the sensor device 800 may include external fluid channels and outlet features, such as grooves. The anchoring member 802 can include one or more fluid outlet ports 806. In some embodiments, the physiological sensor 800 is sized and shaped to be inserted into the anterior chamber of the eye and anchored into eye tissue 804. In one embodiment, the implant is anchored to the trabecular meshwork, thus allowing enhanced drainage of the aqueous humor into Schlemm's canal.

Figure 9:
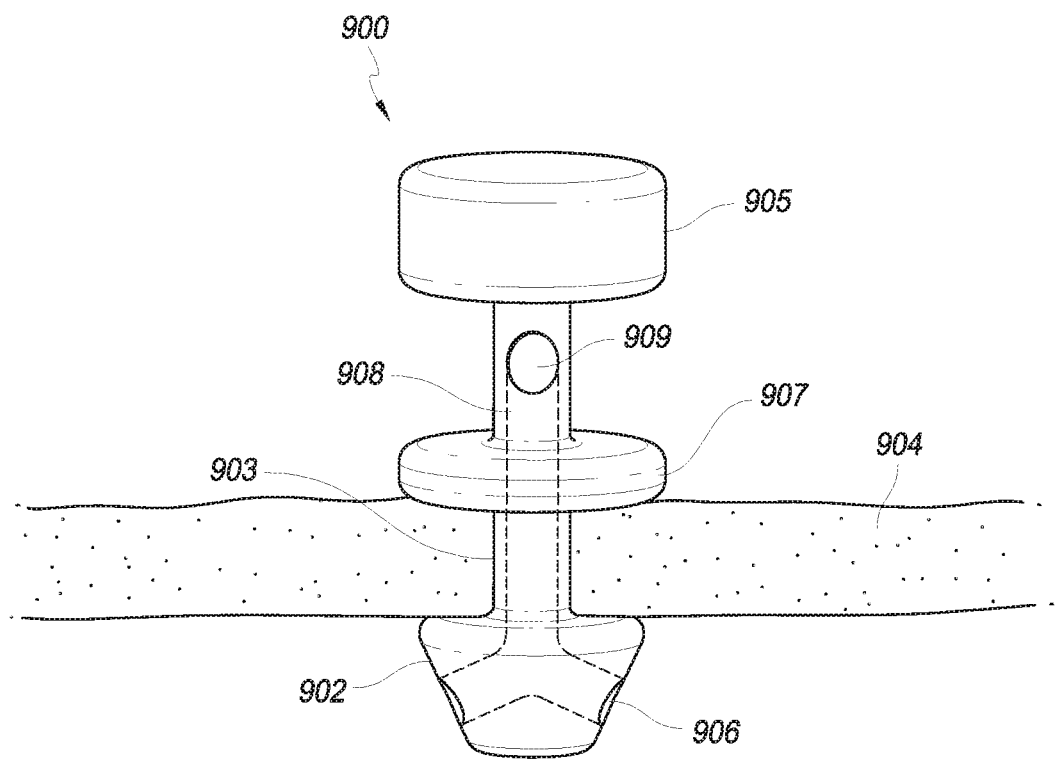
FIG. 9 is a schematic illustration of an implantable intraocular physiological sensor with an anchoring member and a fluid channel that does not pass through an electronics housing portion of the physiological sensor.

FIG. 9 is a schematic illustration of an implantable intraocular physiological sensor 900 with an anchoring member 902 and a fluid channel 908 that does not pass through an electronics housing portion of the physiological sensor. The physiological sensor 900 includes a head portion 905, which in this embodiment, serves as a housing for various electronic components of the sensor (e.g., sensing module, controller module, transmitter, fuel cell, etc.). The head portion 905 is connected to an anchoring member 902 via a stem portion 903.

The stem portion 903 includes one or more fluid inlet ports 909 and a fluid channel 908. The fluid channel 908 extends into the anchoring member 902, which includes one or more fluid outlet ports 906. The stem portion 903 also includes a flange 907 along its length between the head portion 905 and the anchoring member 902. The flange 907, in conjunction with the anchoring member 902, allows the sensor device 900 to be mounted to eye tissue 904 such that the head portion 905 is raised above the tissue 904. The inlet ports 909 of the fluid channel 908 are located in the stem portion 903 between the head portion 905 and the flange 907. Accordingly, the fluid channel 908 need not necessarily pass through the housing (e.g., head portion 905) where electronic components are located. This can be advantageous because locating the fluid channel through the electronics housing may complicate layout of the electronic components within the housing. In the embodiment illustrated in FIG. 9, however, the electronics housing and the fluid channel can be designed substantially independently.

The illustrations in FIGS. 7-10 are schematic in nature. Accordingly, the shape, location, and design of the implants and features of the implants may be different from what is illustrated. For example, the shape and relative sizes of features including but not limited to the head portion, anchoring portion, and flanges can be as illustrated or they may have different shapes. In other embodiments, the cross-sectional shape of the head portion may be circular or polygonal, and the top may be generally flat or curved and it may be larger or smaller in size as compared to the other features of the implant. In other embodiments, an anchor, anchoring portion and/or flange(s) may be of different sizes and shapes, including those disclosed in U.S. Pat. No. 7,857,782, which is hereby incorporated by reference in its entirety. Implants may have more or fewer inlet and/or outlet ports, the inlet and/or outlet ports may be different sizes and/or shapes and at different locations than those illustrated. As stated previously, the sensor device may be configured for placement in the supraciliary or suprachoroidal space by making it elongated in one dimension, and narrow or thin in a second and/or third dimension. The elongated dimension may be in the range of 2-25 mm, while the narrow dimension(s) may be less than 1 mm, and preferably less than 0.5 mm in order to (a) facilitate insertion into the eye through a small gauge insertion needle or cannula; and/or (b) make the device flexible enough to conform to curvature of the anatomy (for example, the curvature of the sclera).

Implants as described herein may include one or more drugs to be delivered to the eye. Devices having drug delivery capabilities allow for a drug to be delivered directly to the eye, and may also allow for targeted delivery to a structure within the eye, such as, for example, the macula, the retina, the ciliary body, the optic nerve, or the vascular supply to certain regions of the eye. Use of a drug eluting implant could also provide the opportunity to administer a controlled amount of drug for a desired amount of time, depending on the pathology. For instance, some pathologies may require drugs to be released at a constant rate for just a few days, others may require drug release at a constant rate for up to several months, still others may need periodic or varied release rates over time, and even others may require periods of no release. Further, implants may serve additional functions once the delivery of the drug is complete. Implants may maintain the patency of a fluid flow passageway within an ocular cavity, they may function as a reservoir for future administration of the same or a different therapeutic agent, or may also function to maintain the patency of a fluid flow pathway or passageway from a first location to a second location, e.g. function as a stent. Conversely, should a drug be required only acutely, an implant may also be made completely biodegradable.

As used herein, "drug" refers generally to one or more drugs that may be administered alone, in combination and/or compounded with one or more pharmaceutically acceptable excipients (e.g. binders, disintegrants, fillers, diluents, lubricants, drug release control polymers or other agents, etc.), auxiliary agents or compounds as may be housed within the implants as described herein. The term "drug" is a broad term that may be used interchangeably with terms such as "therapeutic agent" and "pharmaceutical" or "pharmacological agent" and includes not only so-called small molecule drugs, but also macromolecular drugs, and biologics, including but not limited to proteins, nucleic acids, antibodies and the like, regardless of whether such drug is natural, synthetic, or recombinant. "Drug" may refer to the drug alone or in combination with the excipients described above. "Drug" may also refer to an active drug itself or a prodrug or salt of an active drug.

Following implantation at the desired site within the eye, drug is released from the implant in a targeted and controlled fashion, based on the design of the various aspects of the implant, preferably for an extended period of time. The implant and associated methods disclosed herein may be used in the treatment of pathologies requiring drug administration to the posterior chamber of the eye, the anterior chamber of the eye, or to specific tissues within the eye.

In some embodiments functioning as a drug delivery device alone, the implant is configured to deliver one or more drugs to anterior region of the eye in a controlled fashion while in other embodiments the implant is configured to deliver one or more drugs to the posterior region of the eye in a controlled fashion. In still other embodiments, the implant is configured to simultaneously deliver drugs to both the anterior and posterior region of the eye in a controlled fashion. In yet other embodiments, the configuration of the implant is such that drug is released in a targeted fashion to a particular intraocular tissue, for example, the macula, ciliary body, ciliary processes, ciliary muscles, Schlemm's canal, trabecular meshwork, episcleral veins, lens cortex, lens epithelium, lens capsule, choroid, optic nerve, and/or retina.

In certain embodiments the drug delivery implant may contain one or more drugs which may or may not be compounded with a bioerodible polymer or a bioerodible polymer and at least one additional agent. In still other embodiments, the drug delivery implant is used to sequentially deliver multiple drugs. Additionally, certain embodiments are constructed using different outer shell materials, and/or materials of varied permeability to generate a tailored drug elution profile. Certain embodiments are constructed using different numbers, dimensions and/or locations of orifices in the implant shell to generate a tailored drug elution profile. Certain embodiments are constructed using different polymer coatings and different coating locations on the implant to generate a tailored drug elution profile. Embodiments may elute drug at a constant rate, with a zero-order release profile, or variable elution profile. Some embodiments are designed to stop elution completely or nearly completely for a predetermined period of time (e.g., a "drug holiday") and later resume elution at the same or a different elution rate or concentration. Some such embodiments elute the same therapeutic agent before and after the drug holiday while other embodiments elute different therapeutic agents before and after the drug holiday.

The therapeutic agents utilized with embodiments having drug delivery capabilities, including separate drug delivery implants used in conjunction with a sensor, as well as any implant having a coating comprising a drug may include one or more drugs provided below, either alone or in combination. The drugs utilized may also be the equivalent of, derivatives of, or analogs of one or more of the drugs provided below. The drugs may include but are not limited to pharmaceutical agents including anti-glaucoma medications, ocular agents, antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucleotides, and the like), DNA/RNA vectors, viruses (either wild type or genetically modified) or viral vectors, peptides, proteins, enzymes, extracellular matrix components, and live cells configured to produce one or more biological components. The use of any particular drug is not limited to its primary effect or regulatory body-approved treatment indication or manner of use. Drugs also include compounds or other materials that reduce or treat one or more side effects of another drug or therapeutic agent. As many drugs have more than a single mode of action, the listing of any particular drug within any one therapeutic class below is only representative of one possible use of the drug and is not intended to limit the scope of its use with the ophthalmic implant system.

As discussed above, the therapeutic agents may be combined with any number of excipients as is known in the art. In addition to the biodegradable polymeric excipients discussed above, other excipients may be used, including, but not limited to, benzyl alcohol, ethylcellulose, methylcellulose, hydroxymethylcellulose, cetyl alcohol, croscarmellose sodium, dextrans, dextrose, fructose, gelatin, glycerin, monoglycerides, diglycerides, kaolin, calcium chloride, lactose, lactose monohydrate, maltodextrins, polysorbates, pregelatinized starch, calcium stearate, magnesium stearate, silcon dioxide, cornstarch, talc, and the like. The one or more excipients may be included in total amounts as low as about 1%, 5%, or 10% and in other embodiments may be included in total amounts as high as 50%, 70%, 90% or more. High amounts of excipient are desirable when the drug is in the form of a microscopic pellet or tablet. Additional disclosure on such tablets may be found in International Patent Application Publication No. WO 2010/135369, the disclosure of which is hereby incorporated by reference in its entirety.

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranibizumab (LUCENTIS®) and bevacizumab (AVASTIN®), pegaptanib (MACUGEN®), sunitinib and sorafenib and any of a variety of small-molecule and transcription inhibitors having anti-angiogenesis effect; classes of known ophthalmic drugs, including: glaucoma agents, such as adrenergic antagonists, including for example, beta-blocker agents such as atenolol propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluroometholone, loteprednol, medrysone, fluocinolone acetonide, triamcinolone acetonide, triamcinolone, triamcinolone acetonide, beclomethasone, budesonide, flunisolide, fluorometholone, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as antiallergenics, including, for example, sodium chromoglycate, antazoline, methapyriline, chlorpheniramine, cetrizine, pyrilamine, prophenpyridamine; anti-histamine agents such as azelastine, emedastine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof (such as those disclosed in U.S. Pat. No. 7,759,472 or U.S. patent application Ser. Nos. 12/465,051, 12/564,863, or 12/641,270, each of which is incorporated in its entirety by reference herein), transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoeitin; sodium channels blockers; calcium channel blockers such as nilvadipine or lomerizine; glutamate inhibitors such as memantine nitromemantine, riluzole, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as *ginkgo biloba*; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonists such as WIN55-212-2; free radical scavengers such as methoxypolyethylene glycol thioester (MPDTE) or methoxypolyethlene glycol thiol coupled with EDTA methyl triester (MPSEDE); anti-oxidants such as astaxathin, dithiolethione, vitamin E, or metallocorroles (e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acylethanaolamines and their precursors, N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radiotherapeutic agents; photodynamic therapy agents; gene therapy agents; genetic modulators; auto-immune modulators that prevent damage to nerves or portions of nerves (e.g., demyelination) such as glatimir; myelin inhibitors such as anti-NgR Blocking Protein, NgR (310)ecto-Fc; other immune modulators such as FK506 binding proteins (e.g., FKBP51); and dry eye medications such as cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and. Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; antifungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; antiparasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and triflluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other antibacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; antiplatelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

Figure 10:
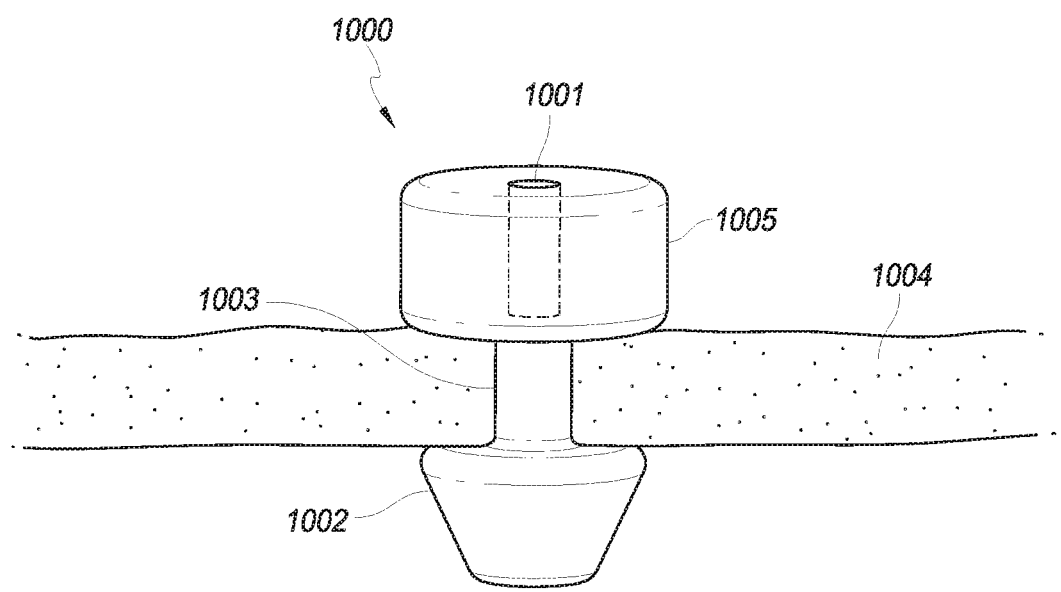
FIG. 10 is a schematic illustration of an implantable intraocular physiological sensor with an anchoring member and a drug repository.

FIG. 10 is a schematic illustration of an implantable intraocular physiological sensor 1000 with an anchoring member 1002 and a drug repository or drug delivery device 1001. The physiological sensor 1000 can include a head portion 1005, which may house various components described herein, such as a sensing module, a controller module, a transmitter, a fuel cell, etc. The head portion 1005 is attached to the anchoring member 1002 by a stem portion 1003. The anchoring member 1002 can be used to mount to the device 1000 in eye tissue, as described herein. The physiological sensor 1000 also includes a drug repository 1001. Although the drug repository or drug delivery device 1001 is illustrated as an opening in the head portion 1005 of the sensor 1000, it can be located at various positions on the device 1000. The drug repository or drug delivery device 1001 can be provided with any of the drugs described herein. In some embodiments, the drug repository or drug delivery device 1001 can either continuously release a drug or release controlled amounts of a drug upon command.

In some embodiments, the physiological sensors described herein can be used to provide a closed monitoring and control system for treating a physiological condition. For example, a target value for a physiological characteristic can be stored in the physiological sensor. The sensor, once implanted in the eye, can then be used to obtain a measured value for the physiological characteristic. The sensor can compare the measured value of the physiological characteristic to the target value of the physiological characteristic and then control an action to reduce the difference between the measured value of the physiological characteristic and the target value of the physiological characteristic. As discussed herein, in some embodiments, the action can be releasing a drug to treat intraocular pressure or regulating the outflow of aqueous humor from the eye.

In some embodiments, the physiological sensor 1000 may be used as a closed continuous IOP monitoring and control system to give a clinician who is managing a glaucoma patient the ability to design and implement an individualized pharmacotherapy regimen that is controlled by the physiological sensor 1000 based on predetermined IOP targets set by the clinician. Generally, a physician managing a glaucoma patient can establish a target level of intraocular pressure which he or she feels is suited to the patient to reduce the risk of disease progression. In selecting the target pressure, the physician may take into account a number of factors, including but not limited to, current/baseline IOP, family history, optic nerve head status, retinal nerve fiber layer evaluation, and visual field effects. Although numerous studies have found that lower pressures reduce the risk of progression, the clinician tends to select a target pressure that strikes an appropriate balance between risk of progression and the side effects and morbidity associated with the interventions required to reach and maintain the target pressure.

With a closed continuous IOP monitoring system, the physician or other user could select a target pressure and program the system to instruct a drug delivery device to administer a pre-defined dose of, for example, a hypotensive medication in response to specific IOP measurement criteria. Additionally, or alternatively, the system could instruct the patient to administer a specific topical medication in response to specific outputs. This allows the system to administer only the amount of drug necessary to consistently maintain IOP at or below the target pressure.

For example, the physician could select a target pressure of 16 mm Hg for a patient. The patient can be implanted (e.g., at the trabecular meshwork) with a device such as intraocular physiological sensor 1000 that continuously administers a therapeutic level of a drug, such as a prostaglandin analogue. The patient can also be implanted with a device in the suprachoroidal space that contains a drug such as an alpha agonist. However, this second drug may only be delivered in the event that the patient's average IOP, as measured by the implanted device, exceeds 18 mm Hg for a set period of time. In another example, a physician may select a target pressure, such as 18 mm Hg. The patient can be implanted with a device in the trabecular meshwork that continuously administers a therapeutic level of a drug, such as a prostaglandin analogue. The implanted monitoring device may communicate to the patient (e.g., via an external device worn by the patient) to administer a topical dose of a drug such as timolol in the event that the patient's average IOP exceeds, for example, 21 mm Hg for a period of time, such as six hours. In another example, a physician may select a target pressure of, for example, 18 mm Hg. The patient can be implanted with a device in the trabecular meshwork that administers a dose of a drug, such as prostaglandin analogue, only when the patient's IOP exceeds the target value for some set period of time.

In addition to the closed continuous IOP monitoring and control system that provides for controlled management of IOP with drugs, a similar closed continuous IOP monitoring and control system could be provided using a stent to manage IOP by regulating the outflow of aqueous humor. In such embodiments, the outflow of the stent and/or the release of a drug can be controlled based upon, for example, intraocular pressure measurements from the physiological sensor in conjunction with a target intraocular pressure value that may be programmed into the sensor by a clinician.

A similar closed continuous monitoring and control system could also be implemented with glucose concentration measurements. For example, a clinician or the patient could set a target glucose level. The implanted intraocular physiological sensor could then monitor glucose concentration levels and control an insulin pump (e.g., with a wireless command interface) to administer insulin based on a comparison between the measured glucose value and the target value. Alternatively, and/or additionally, the physiological sensor could communicate to the patient (e.g., via an external device worn by the patient) a notification to eat or to exercise based on the comparison between the measured glucose value and the target value.

Various embodiments of implants disclosed herein may be implanted by an ab interno procedure or an ab externo procedure. The "ab interno" procedure is herein intended to mean any procedure that creates an opening from the anterior chamber into eye tissue within or forming a boundary of the anterior chamber, usually in a backward direction. This ab interno procedure may be initiated through the scleral wall or cornea wall into the anterior chamber as a first step. The term "ab externo" procedure is herein intended to mean any procedure that creates an opening on the scleral wall and proceeds inwardly toward the anterior chamber. For example, in some "ab externo" procedures, an instrument is passed through or contacts Schlemm's canal before entering trabecular meshwork and approaching the anterior chamber. In some embodiments, ab externo procedures may pass through some or all of the thickness of the scleral wall in order to position a sensor device inside the eye or within the scleral wall. A less-invasive ab externo procedure can be accomplished by tunneling through scleral tissue with a needle or cannula such that the tip of the needle or cannula accesses the anterior chamber or the suprachoroidal space. A sensor device may then be advanced through the needle or cannula to be at least partially located within the anterior chamber, or at least partially located within the suprachoroidal space. After delivery of the sensor device within the eye, the needle or cannula is withdrawn, leaving a self-sealing track through the sclera. Implantation by this method may result in some or all of the sensor device residing within scleral tissue, or between the sclera and the conjunctiva.

Implants may be placed in the eye using an applicator, such as a pusher, guidewire, forceps or other suitable device. The applicator may also be a delivery instrument including but not limited to that disclosed in U.S. Application Publication No. 2002/0133168 or that disclosed in U.S. Pat. No. 7,331,984 which has energy stored in the instrument for delivering one or more implants. The contents of these two documents are hereby incorporated by reference herein in their entireties.

Some embodiments of applicator have trephining capability, wherein a cutting or tissue penetration feature or mechanism forms part of the applicator for purposes of making a hole or opening in eye tissue to allow for implanting and/or securing an implant within the eye. In some embodiments, an implant may be self-trephining such that it makes its own opening.

One embodiment of delivery apparatus includes a handpiece, an elongate body, a holder and a delivery mechanism. In some embodiments, the delivery mechanism is an actuator. The handpiece has a distal end and a proximal end. The elongate body is connected to the distal end of the handpiece. At least the distal portion of the elongate body is sized and configured to be placed through a incision in the sclera or cornea, including at or near the limbus, and into an anterior chamber of the eye. The holder is attached to the distal portion of the elongate tip and is configured to hold and release the implant. The deployment mechanism or actuator is on the handpiece and serves to release the implant from the holder.

In some embodiments, the holder comprises a clamp. The clamp may comprise a plurality of claws configured to exert a clamping force onto at least a portion, usually the proximal portion, of the implant. The holder may also comprise one or more flanges, bumps or other raised regions which utilize friction to hold the device or which engage a corresponding feature on the implant. The holder may also comprise a recessed area or groove at or near the end of the elongate body for retaining an implant or a portion thereof.

In some embodiments, the apparatus further comprises a spring within the handpiece that is configured to be loaded when the one or more implants are being held by the holder, the spring being at least partially unloaded upon actuating the actuator, allowing for release of an implant from the holder.

The deployment mechanism of the delivery apparatus may include a push-pull type plunger, push button or trigger that is operated to cause delivery of an implant, such as by releasing at least some tension from a spring in an actuator mechanism or by causing at least one portion of the delivery device to move relative to another portion of the delivery device and/or an implant. In some embodiments, an actuator may be used to operate a trocar or cutting device to allow for consistent and predictable formation of an opening in eye tissue.

The elongate portion of the device may be flexible or made of a flexible material, such as a flexible wire. The distal portion can have a deflection range, preferably of about 45 degrees from the long axis of the handpiece. The elongate portion of the device may be curved to aid in reaching the anterior angle on the opposite side of the eye from where the opening is made into the anterior chamber. The delivery apparatus can further comprise an irrigation port in the elongate tip.

In some embodiments, the delivery device is adapted to deliver more than one implant into the eye without having to remove the device from the eye between implantations. The implants delivered may be any combination of sensor, drainage device, micropump, drug delivery device and any combination of the foregoing, including devices that may include one or more of the foregoing functions. For example, a delivery device may deliver a sensor-type implant and a combination drainage/drug delivery implant, an IOP sensor and two drainage implants, a IOP sensor and a drug delivery implant, and the like. A device for delivering multiple implants may include an elongate body sized to be introduced into an eye through an incision in the eye and a plurality of implants positioned on or in the elongate body. The elongate body may further comprise an actuator that serially dispenses the implants from the elongate body for implanting in eye tissue.

A method of implanting one or more implants includes inserting an instrument into an eye through an incision, and utilizing the instrument to deliver a first implant into or onto eye tissue at a first location. Other embodiments include utilizing the instrument to deliver a second implant into or onto eye tissue at a second location, without removing the instrument from the eye between the deliveries of the implants.

The incision may be made into the sclera or cornea, including at or near the limbus. In some embodiments, the incision is small so as to be self-sealing. In other embodiments, one or two stitches may be needed to close the opening once the implantation procedure is completed and the delivery device removed from the eye. In some embodiments, the incision is about 1 mm in length. The placement and implantation of the implant(s) may then be performed using a gonioscope or other imaging equipment used in eye surgery, as known in the art.

During implantation, the delivery instrument may be advanced through an insertion site or incision and advanced to desired eye tissue. In some embodiments, the advancement is either transocularly or posteriorly into the anterior chamber angle. Using the anterior chamber angle as a reference point, the delivery instrument can be advanced further in a generally posterior direction to drive the implant into the iris, inward of the anterior chamber angle. The delivery device may be used to implant one or more implants at any location in the eye, including the trabecular meshwork, Schlemm's canal, supraciliary space, suprachoroidal space, and the like.

Optionally, based on the implant structure, the implant may be laid within the anterior chamber angle, taking on a curved shape to match the annular shape of the anterior chamber angle. It is preferred, however, that an implant be secured to tissue, such as by using an anchor, adhesive, friction or other force, or at least not be free to move within the anterior chamber so as to minimize damage to delicate eye tissue such as the corneal endothelium.

Once the delivery device and implant are at the desired location in the eye, an opening may be made in ocular tissue. This may be done, for example, using the distal end of the elongate portion of the delivery device or with a self-trephining implant. The implant is then delivered to the tissue. Delivery may be done by using a deployment mechanism. For example, a pusher tube may be advanced axially toward the distal end of the delivery instrument, such that as the pusher tube is advanced, the implant is also advanced. When the implant is in the desired position, the delivery instrument may be retracted, leaving the implant in the eye tissue. Another implant may then be implanted at another location in the eye, or the delivery device may be removed from the eye.

In other embodiments, the delivery instrument is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument. Alternatively, the device may be implanted by using the actuator to drive an implant into tissue using stored energy, such as from a spring or other energy storage means.

In one embodiment, the implant is affixed to intraocular tissue. In one embodiment, this additional affixation may be performed with a biocompatible adhesive. In other embodiments, one or more sutures may be used or one or more tissue anchors may be used. In another embodiment, the implant is held substantially in place via the interaction of the implant body's outer surface and the surrounding tissue of the anterior chamber angle. A device may also use some combination of the foregoing affixation methods.

Various intraocular physiological sensors are described herein. As further described herein, in some embodiments, such sensors include fluid channels, or other types of shunts. As discussed herein, in some embodiments, the sensor/shunt is inserted from a site transocularly situated from the implantation site. The delivery instrument can be sufficiently long to advance the sensor/shunt transocularly from the insertion site across the anterior chamber to the implantation site. At least a portion of the instrument can be flexible. Alternatively, the instrument can be rigid. The instrument can comprise a plurality of members longitudinally moveable relative to each other. In some embodiments, at least a portion of the delivery instrument is curved or angled. In some embodiments, a portion of the delivery instrument is rigid and another portion of the instrument is flexible.

In some embodiments, the delivery instrument has a distal curvature. The distal curvature of the delivery instrument may be characterized as a radius of approximately 10 to 30 mm, and preferably about 20 mm.

In some embodiments, the delivery instrument has a distal angle. The distal angle may be characterized as approximately 90 to 170 degrees relative to an axis of the proximal segment of the delivery instrument, and preferably about 145 degrees. The angle can incorporate a small radius of curvature at the "elbow" so as to make a smooth transition from the proximal segment of the delivery instrument to the distal segment. The length of the distal segment may be approximately 0.5 to 7 mm, and preferably about 2 to 3 mm.

In some embodiments, the instruments have a sharpened forward end and are self-trephinating, i.e., self-penetrating, so as to pass through tissue without pre-forming an incision, hole or aperture. Alternatively, a trocar, scalpel, or similar instrument can be used to pre-form an incision in the eye tissue before passing the sensor/shunt into such tissue.

For delivery of some embodiments of the ocular sensor/shunt, the instrument can have a sufficiently small cross section such that the insertion site self seals without suturing upon withdrawal of the instrument from the eye. An outer diameter of the delivery instrument preferably is no greater than about 18 gauge and is not smaller than about 32 gauge. For clarification and avoidance of doubt, all delivery devices disclosed herein may be used to deliver any implant disclosed herein, including, but not limited to, a sensor, a shunt or drainage device, and combinations thereof, to any portion of the eye, and preferably those that may be accessed from the anterior chamber. Delivery devices may also deliver more than one device, preferably without having to remove the delivery device from the eye between implantations.

For delivery of some embodiments of the ocular sensor/shunt, the incision in the corneal tissue is preferably made with a hollow needle through which the sensor/shunt is passed. The needle has a small diameter size (e.g., 18 or 19 or 20 or 21 or 22 or 23 or 24 or 25 or 26 or 27 or 28 or 29 or 30 or 31 or 32 gauge) so that the incision is self sealing and the implantation occurs in a closed chamber with or without viscoelastic. A self-sealing incision also can be formed using a conventional "tunneling" procedure in which a spatula-shaped scalpel is used to create a generally inverted V-shaped incision through the cornea. In a preferred mode, the instrument used to form the incision through the cornea remains in place (that is, extends through the corneal incision) during the procedure and is not removed until after implantation. Such incision-forming instrument either can be used to carry the ocular sensor/shunt or can cooperate with a delivery instrument to allow implantation through the same incision without withdrawing the incision-forming instrument. Of course, in other modes, various surgical instruments can be passed through one or more corneal incisions multiple times.

Once into the anterior chamber, a delivery instrument can be advanced from the insertion site transocularly into the anterior chamber angle and positioned at a location near the scleral spur. Using the scleral spur as a reference point, the delivery instrument can be advanced further in a generally posterior direction to drive the sensor/shunt into eye tissue at a location just inward of the scleral spur toward the iris. The placement and implantation of the sensor/shunt can be performed using a gonioscope or other conventional imaging equipment. The delivery instrument preferably is used to force the sensor/shunt into a desired position by application of a continual implantation force, by tapping the sensor/shunt into place using a distal portion of the delivery instrument, or by a combination of these methods. Once the sensor/shunt is in the desired position, it may be further seated by tapping using a distal portion of the delivery instrument.

The delivery instrument can include an open distal end with a lumen extending therethrough. Positioned within the lumen is preferably a pusher tube that is axially movable within the lumen. The pusher tube can be any device suitable for pushing or manipulating the sensor/shunt in relation to the delivery instrument, such as, for example, but without limitation a screw, a rod, a stored energy device such as a spring. A wall of the delivery instrument preferably extends beyond pusher tube to accommodate placement within the lumen of a sensor/shunt. The sensor/shunt can be secured in position. For example, the sensor/shunt can be secured by viscoelastic or mechanical interlock with the pusher tube or wall. When the sensor/shunt is brought into position adjacent the tissue in the anterior chamber angle, the pusher tube is advanced axially toward the open distal end of the delivery instrument. As the pusher tube is advanced, the sensor/shunt is also advanced. When the sensor/shunt is advanced through the tissue and such that it is no longer in the lumen of the delivery instrument, the delivery instrument is retracted, leaving the sensor/shunt in the eye tissue.

Some embodiments can include a spring-loaded or stored-energy pusher system. The spring-loaded pusher preferably includes a button operably connected to a hinged rod device. The rod of the hinged rod device engages a depression in the surface of the pusher, keeping the spring of the pusher in a compressed conformation. When the user pushes the button, the rod is disengaged from the depression, thereby allowing the spring to decompress, thereby advancing the pusher forward.

In some embodiments, an over-the wire system is used to deliver the sensor/shunt. The sensor/shunt can be delivered over a wire. Preferably, the wire is self-trephinating. The wire can function as a trocar. The wire can be superelastic, flexible, or relatively inflexible with respect to the sensor/shunt. The wire can be pre-formed to have a certain shape. The wire can be curved. The wire can have shape memory, or be elastic. In some embodiments, the wire is a pull wire. The wire can be a steerable catheter.

In some embodiments, the wire is positioned within a lumen in the sensor/shunt. The wire can be axially movable within the lumen. The lumen may or may not include valves or other flow regulatory devices.

In some embodiments, the delivery instrument comprises a trocar. The trocar may be angled or curved. The trocar can be rigid, semi-rigid or flexible. In embodiments where the trocar is stiff, the sensor/shunt can be, but need not be relatively flexible. The diameter of the trocar can be about 0.001 inches to about 0.01 inches. In some embodiments, the diameter of the trocar is 0.001, 0.002, 0.004, 0.005, 0.006, 0.007, 0.008, 0.009, or 0.01 inches.

In some embodiments, delivery of the sensor/shunt is achieved by applying a driving force at or near the distal end of the sensor/shunt. The driving force can be a pulling or a pushing applied generally to the end of the sensor/shunt.

The instrument can include a seal to prevent aqueous humor from passing through the delivery instrument and/or between the members of the instrument when the instrument is in the eye. The seal can also aid in preventing backflow of aqueous humor through the instrument and out the eye. Suitable seals for inhibiting leakage include, for example, an o-ring, a coating, a hydrophilic agent, a hydrophobic agent, and combinations thereof. The coating can be, for example, a silicone coat such as MDX™ silicone fluid. In some embodiments, the instrument is coated with the coating and a hydrophilic or hydrophobic agent. In some embodiments, one region of the instrument is coated with the coating plus the hydrophilic agent, and another region of the instrument is coated with the coating plus the hydrophobic agent. The delivery instrument can additionally comprise a seal between various members comprising the instrument. The seal can comprise a hydrophobic or hydrophilic coating between slip-fit surfaces of the members of the instrument. The seal can be disposed proximate of the drainage sensor/shunt when carried by the delivery instrument. Preferably, the seal is present on at least a section of each of two devices that are machined to fit closely with one another.

In some embodiments, the delivery instrument can include a distal end having a beveled shape. The delivery instrument can include a distal end having a spatula shape. The beveled or spatula shape can have a sharpened edge. The beveled or spatula shape can include a recess to contain the sensor/shunt. The recess can include a pusher or other suitable means to push out or eject the sensor/shunt.

The delivery instrument further can be configured to deliver multiple shunts. In some embodiments, when multiple shunts are delivered, the shunts can be arranged in tandem, as described in greater detail below.

For delivery of some embodiments of the ocular sensor/shunt, the implantation occurs in a closed chamber with or without viscoelastic. The shunts may be placed using an applicator, such as a pusher, or they may be placed using a delivery instrument having energy stored in the instrument, such as disclosed in U.S. Patent Publication 2004/0050392, filed Aug. 28, 2002, the entirety of which is incorporated herein by reference and made a part of this specification and disclosure. In some embodiments, fluid may be infused through the delivery instrument or another instrument used in the procedure to create an elevated fluid pressure at the distal end of the sensor/shunt to ease implantation.

In some embodiments, the sensor/shunt is implanted through the fibrous attachment of the ciliary muscle to the sclera. This fibrous attachment zone extends about 0.5 mm posteriorly from the scleral spur, as shown between the two arrows (1020) in FIG. 11.

In some embodiments it is desirable to deliver the sensor/shunt ab interno across the eye, through a small incision at or near the limbus. The overall geometry of the system makes it advantageous that the delivery instrument incorporates a distal curvature, or a distal angle. In the former case, the sensor/shunt can be flexible to facilitate delivery along the curvature or can be more loosely held to move easily along an accurate path. In the latter case, the sensor/shunt can be relatively rigid. The delivery instrument can incorporate a sensor/shunt advancement element (e.g. pusher) that is flexible enough to pass through the distal angle.

In some embodiments, during clinical use, the sensor/shunt and delivery instrument can be advanced together through the anterior chamber 32 from an incision at or near the limbus, across the iris, and through the ciliary muscle attachment until the sensor/shunt outlet portion is located in the uveoscleral outflow pathway (e.g. exposed to the suprachoroidal space 34 defined between the sclera 38 and the choroid 40). The operator can then simultaneously push on a pusher device while pulling back on the delivery instrument, such that the sensor/shunt outlet portion maintains its location in the uveoscleral outflow pathway. The sensor/shunt is released from the delivery instrument, and the delivery instrument is retracted proximally. The delivery instrument then can be withdrawn from the anterior chamber through the incision.

In some embodiments, a viscoelastic can be injected into the suprachoroidal space to create a chamber or pocket between the choroid and sclera which can be accessed by a sensor/shunt. Such a pocket could expose more of the choroidal and scleral tissue area, and increase uveoscleral outflow, causing a lower IOP. In some embodiments, the viscoelastic material can be injected with a 25 or 27G cannula, for example, through an incision in the ciliary muscle attachment or through the sclera (e.g. from outside the eye). The viscoelastic material can also be injected through the sensor/shunt itself either before, during or after implantation is completed.

In some embodiments, a hyperosmotic agent can be injected into the suprachoroidal space. Such an injection can delay IOP reduction. Thus, hypotony can be avoided in the acute postoperative period by temporarily reducing choroidal absorption. The hyperosmotic agent can be, for example glucose, albumin, HYPAQUE™ medium, glycerol, or poly(ethylene glycol). The hyperosmotic agent can breakdown or wash out as the patient heals, resulting in a stable, acceptably low IOP, and avoiding transient hypotony.

Figure 11:
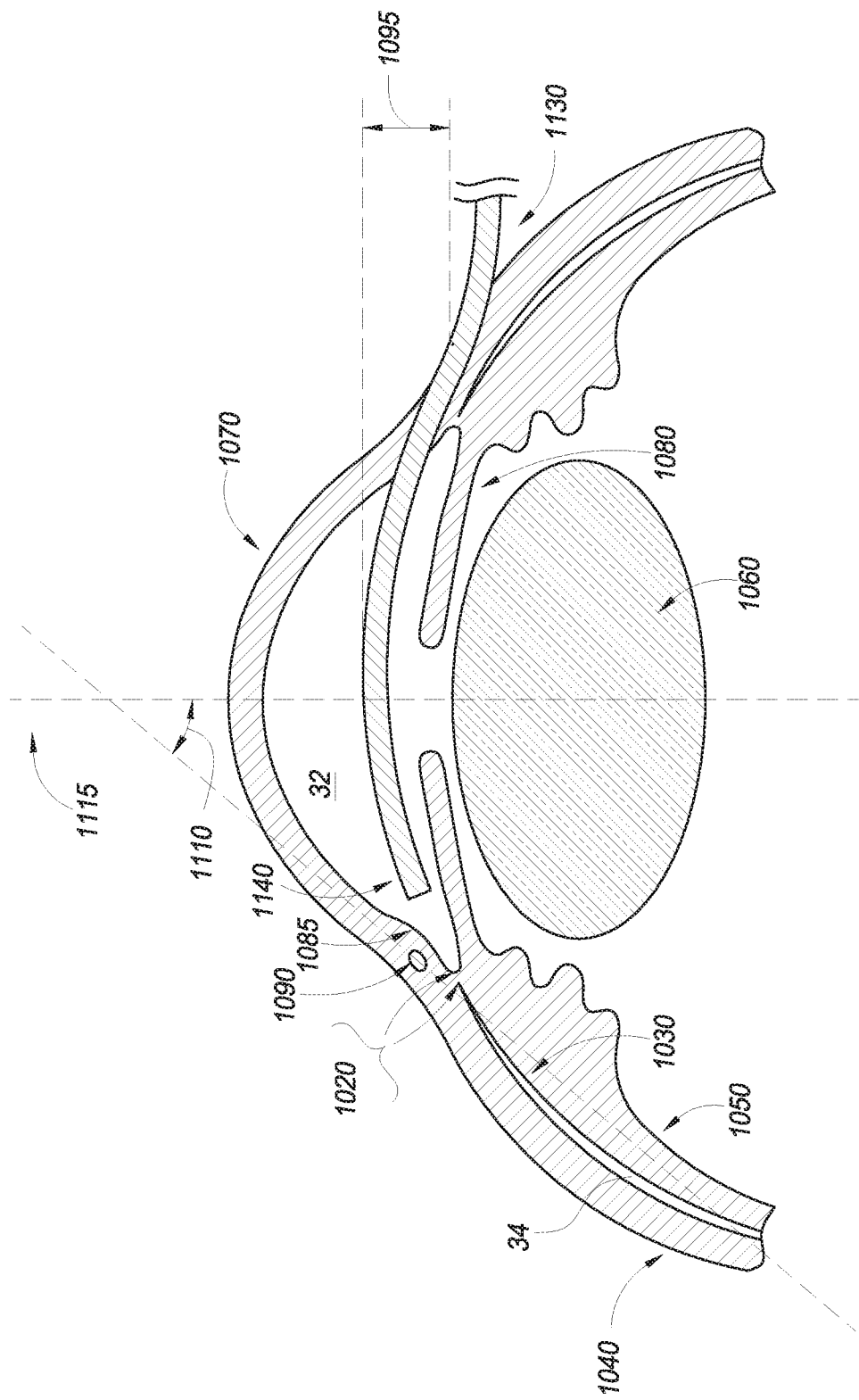
FIG. 11 illustrates a schematic cross-sectional view of an eye with a delivery device being advanced across the anterior chamber.

FIG. 11 shows a meridional section of the anterior segment of the human eye and schematically illustrates another embodiment of a delivery instrument 1130 that can be used with embodiments of shunts described herein. In FIG. 11, arrows 1020 show the fibrous attachment zone of the ciliary muscle 1030 to the sclera 1040. The ciliary muscle is part of the choroid 1050. The suprachoroidal space 34 is the interface between the choroid and the sclera. Other structures in the eye include the lens 1060, the cornea 1070, the anterior chamber 32, the iris 1080, and Schlemm's canal 1090.

In some embodiments, it is desirable to implant a sensor/shunt through the fibrous attachment zone, thus connecting the anterior chamber to the uveoscleral outflow pathway, in order to reduce the intraocular pressure in glaucomatous patients. In some embodiments, it is desirable to deliver the sensor/shunt with a device that traverses the eye internally (ab interno), through a small incision in the limbus.

The delivery instrument/sensor/shunt assembly may be passed between the iris and the cornea to reach the iridocorneal angle. Therefore, the height of the delivery instrument/sensor/shunt assembly (dimension 1095 in FIG. 11) preferably is less than about 3 mm, and more preferably less than 2 mm.

The suprachoroidal space between the choroid and the sclera generally forms an angle 1110 of about 55 degrees with the optical axis 1115 of the eye. This angle, in addition to the height requirement described in the preceding paragraph, are features to consider in the geometrical design of the delivery instrument/sensor/shunt assembly.

Figure 12:
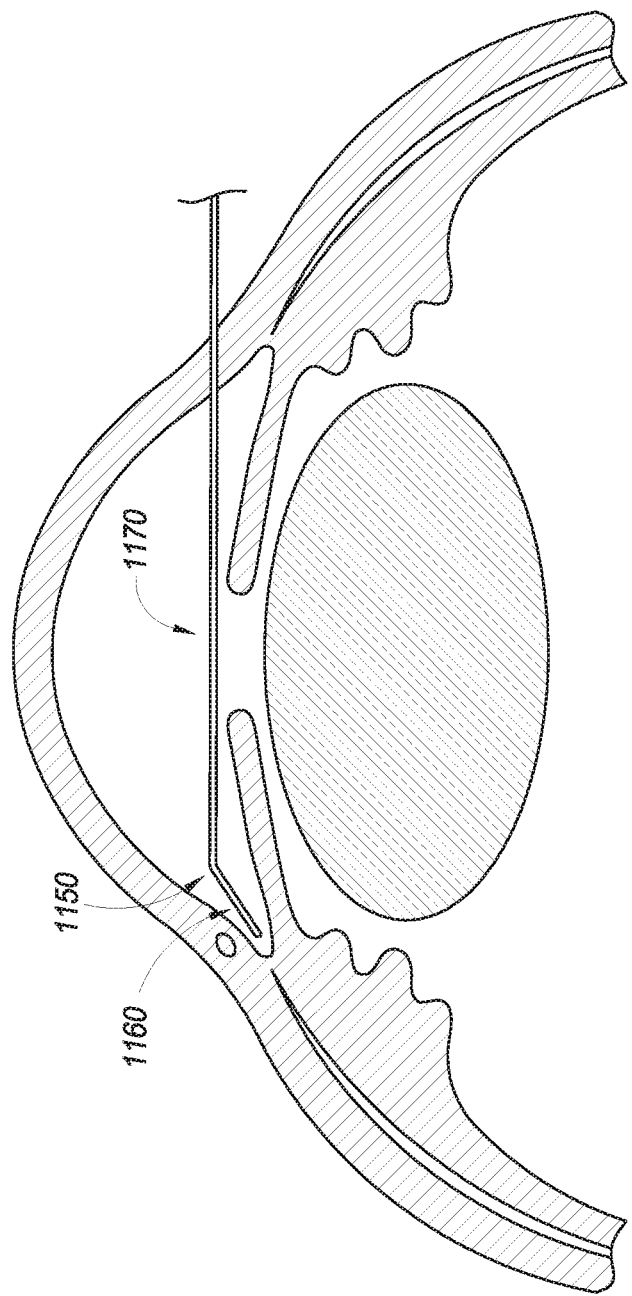
FIG. 12 illustrates a schematic cross-sectional view of an eye with a delivery device being advanced across the anterior chamber.

The overall geometry of the system makes it advantageous that the delivery instrument 1130 incorporates a distal curvature 1140, as shown in FIG. 11, or a distal angle 1150, as shown in FIG. 12. The distal curvature (FIG. 11) is expected to pass more smoothly through the corneal or scleral incision at the limbus. However, the sensor/shunt preferably is curved or flexible in this case. Alternatively, in the design of FIG. 12, the sensor/shunt may be mounted on the straight segment of the delivery instrument, distal of the "elbow" or angle 1150. In this case, the sensor/shunt may be straight and relatively inflexible, and the delivery instrument can incorporate a delivery mechanism that is flexible enough to advance through the angle. In some embodiments, the sensor/shunt is a rigid tube, provided that the sensor/shunt is no longer than the length of the distal segment 1160.

The distal curvature 1140 of delivery instrument 1130 may be characterized as a radius of approximately 10 to 30 mm, and preferably about 20 mm. The distal angle of the delivery instrument depicted in FIG. 12 may be characterized as approximately 90 to 170 degrees relative to an axis of the proximal segment 1170 of the delivery instrument, and preferably about 145 degrees. The angle incorporates a small radius of curvature at the "elbow" so as to make a smooth transition from the proximal segment 1170 of the delivery instrument to the distal segment 1160. The length of the distal segment 1160 may be approximately 0.5 to 7 mm, and preferably about 2 to 3 mm.

Figure 13:
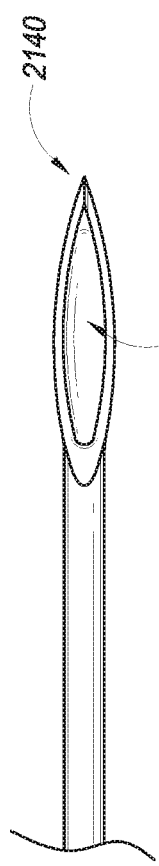
FIG. 13 illustrates a delivery device in accordance with embodiments disclosed herein.
Figure 14A:
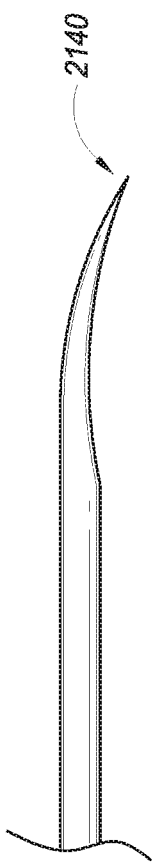
FIGS. 14A-B illustrate side views of the delivery device of FIG. 13.
Figure 14B:
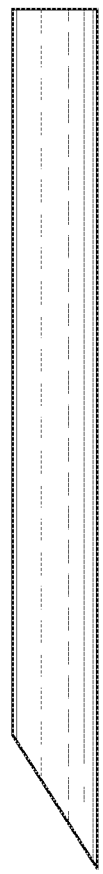

FIGS. 13, 14A and 14B show an example of a delivery instrument for a sensor/shunt. In some embodiments, the sensor/shunt is delivered through a needle with a cutting tip 2140. The sensor/shunt can be loaded inside of the shaft of the needle for delivery through the eye. The needle can be curved on the side of the needle opposite to the beveled opening 2150, as illustrated in FIG. 14A. This allows the curved part of the needle to take a "downward" direction without appreciably affecting the effective height of the device. This geometry can be advantageous for passage through the anterior chamber between the iris and the cornea. At the same time, the curve permits the sharp tip of the needle to follow the angle of the ciliary muscle/sclera interface (angle 1110 shown in FIG. 11). Further, the design of the curved tip as shown in FIG. 14A can limit the depth of the dissection of the ciliary muscle from the sclera to the minimum depth necessary to cut through the fibrous attachment tissue. This depth is estimated to be less than about 0.5 mm. In addition, the curvature of the tip act as a baffle to redirect the sensor/shunt as it is pushed distally outward through the needle. In other embodiments, the needle cutting tip is straight, as illustrated in FIG. 14B.

Figure 15:
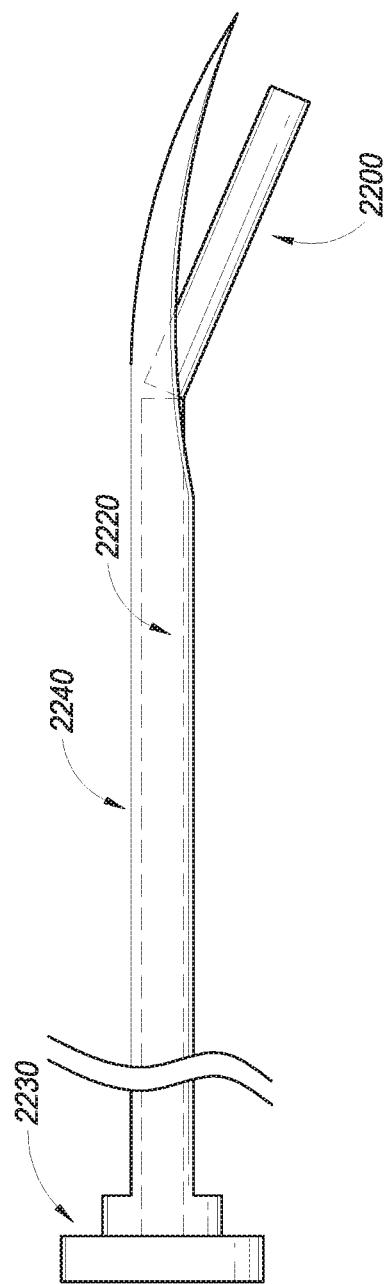
FIG. 15 illustrates a delivery device in accordance with embodiments disclosed herein.

FIG. 15 shows another embodiment of a system that can be used to perform a variety of methods or procedures. The sensor/shunt 2200 is deflected "downward" at an angle that parallels the suprachoroidal space. The depth of insertion can be determined by the length of the pushrod 2220, whose travel can be limited by the stop 2230. It is preferred that the pushrod ends at the proximal edge of the opening of the needle 2240. In this way, the sensor/shunt will not be pushed below the anterior surface of the ciliary muscle.

Figure 16:
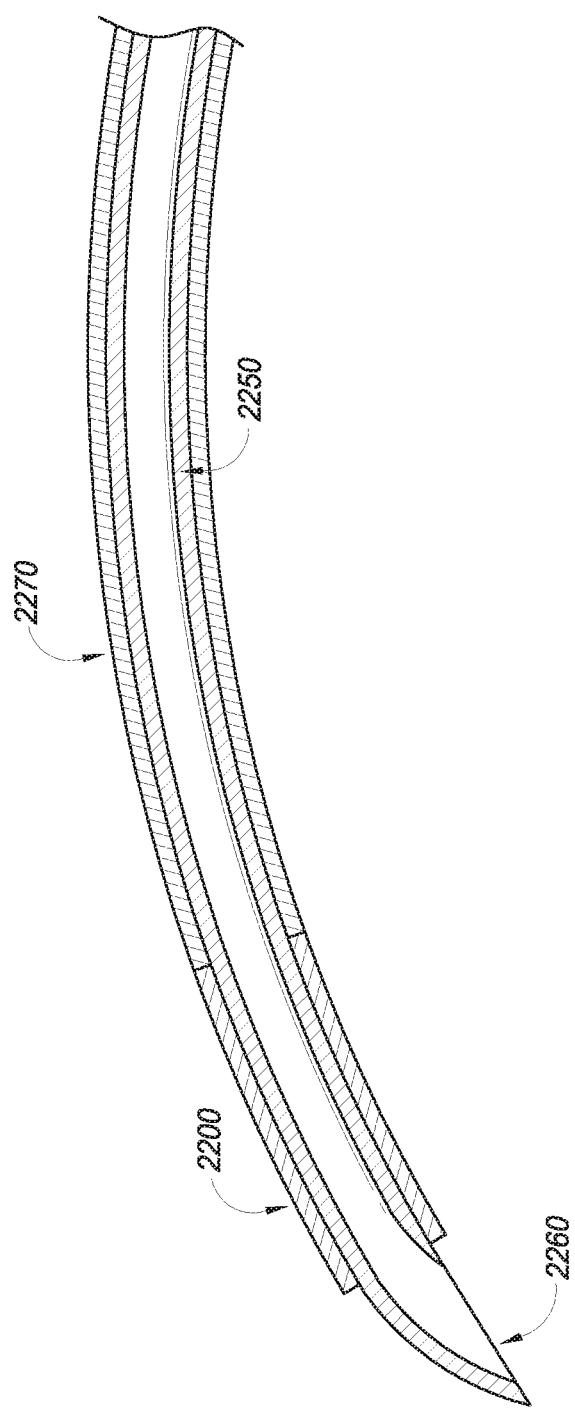
FIG. 16 illustrates a cross-sectional view of an embodiment of a delivery device.

FIG. 16 shows another embodiment of a system that can be used to perform a variety of methods or procedures. In the illustrated embodiment, the sensor/shunt 2200 is mounted on a curved or angled shaft 2250. In some embodiments, both the sensor and the shunt are mounted on the shaft. In other embodiments, while the sensor may be connected to the shunt, only the shunt is mounted on the shaft (e.g., the sensor may be tethered to the shunt, which is mounted on the shaft). The shaft 2250 can be tubular (as shown), or solid and the distal end 2260 can be sharpened. The sensor/shunt 2200 can be curved with approximately the same radius as the delivery device, so that the sensor/shunt can be relatively stiff and still slide along the shaft. In some embodiments, a pusher tube 2270 causes the sensor/shunt to slide distally along the shaft and be released. In operation in some embodiments, the sharpened end 2260 makes an incision in the fibrous tissue attaching the ciliary muscle and the sclera. In some embodiments, the distance between the sharpened tip 2260 and the distal end of the sensor/shunt determines how deeply the tissue may be incised. After making the cut, the operator can advance the pusher tube 2270 while holding the mounting shaft 2250 fixed. This action causes the sensor/shunt 2200 to be advanced into the incision. The distance of sensor/shunt advance can be determined by the length of the pusher tube 2270, whose travel can be limited by a stop, as depicted in FIG. 15.

Further embodiments of the invention incorporate injection of viscoelastic through the sensor/shunt or through the shaft 2250 in order to accomplish posterior dissection of the suprachoroidal tissue, thereby creating a volumetric chamber or reservoir for aqueous humor. In addition or in the alternative, therapeutic agents (e.g., a hyperosmatic agent) can be delivered into the suprachoroidal space through the sensor/shunt 2220 or through the shaft 2250.

Figure 17:
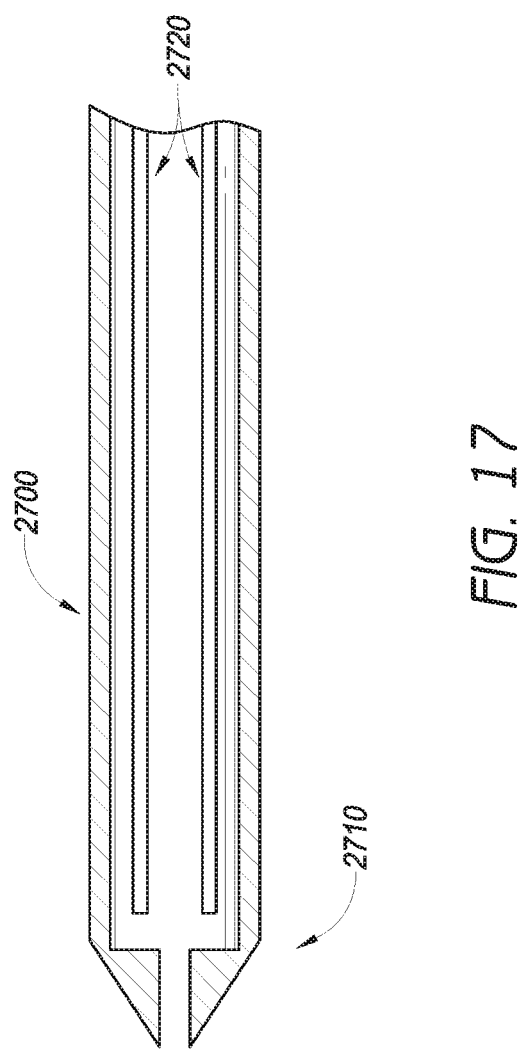
FIG. 17 illustrates a cross-sectional view of an embodiment of a delivery device.

FIG. 17 shows another embodiment of a system that can be used to perform a variety of methods or procedures. Delivery of the sensor/shunt 2700 is achieved by applying a driving force at or near the distal end 2710 of the sensor/shunt 2700 using, for example, a pusher 2720. The driving force can be a pushing force applied to the distal end 2710 of the sensor/shunt 2700. The delivery device alternatively can extend through or around the sensor/shunt to supply a pulling force to draw the sensor/shunt through tissue.

Figure 18:
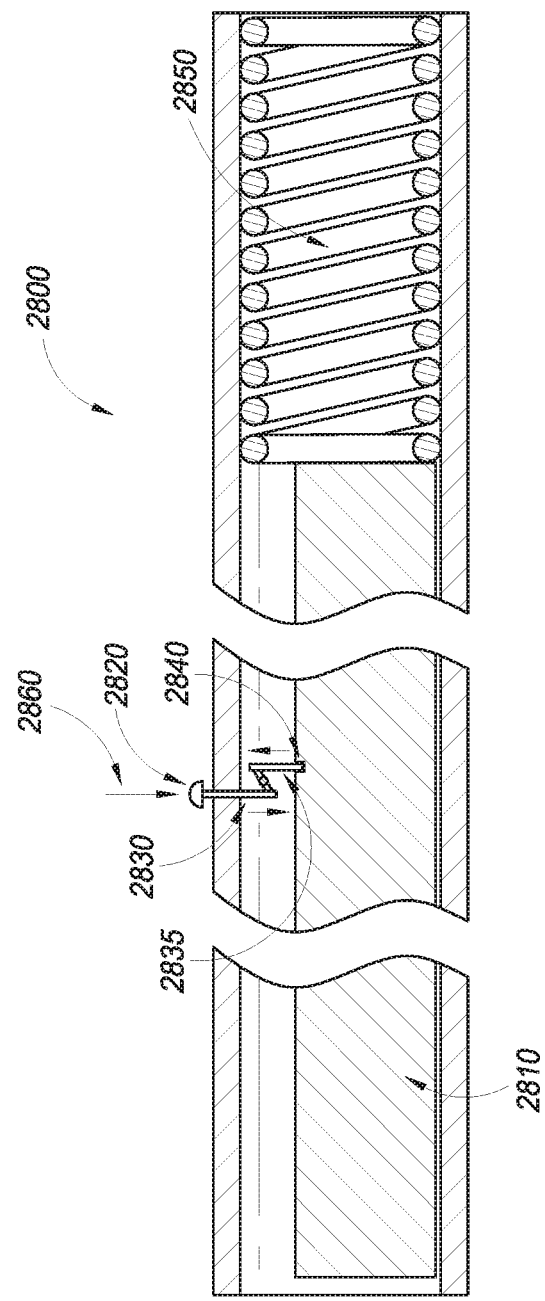
FIG. 18 illustrates a cross-sectional view of an embodiment of a delivery device.

FIG. 18 shows another embodiment of a system 2800 that can be used to perform a variety of methods or procedures. A spring-loaded pusher system 2800 can be used for delivery of a sensor/shunt. The spring-loaded pusher 2810 preferably includes a button 2820 operably connected to a hinged rod device 2830. The distal portion 2835 of the hinged rod device 2830 engages a depression 2840 in the surface of the pusher 2810, keeping the spring 2850 of the pusher 2810 in a compressed conformation. When the user pushes downwards 2860 on the button 2820, the distal portion 2835 of the hinged rod device 2830 is disengaged from the depression 2840, thereby allowing the spring 2850 to decompress, thereby advancing the pusher 2810 forward.

Figure 19:
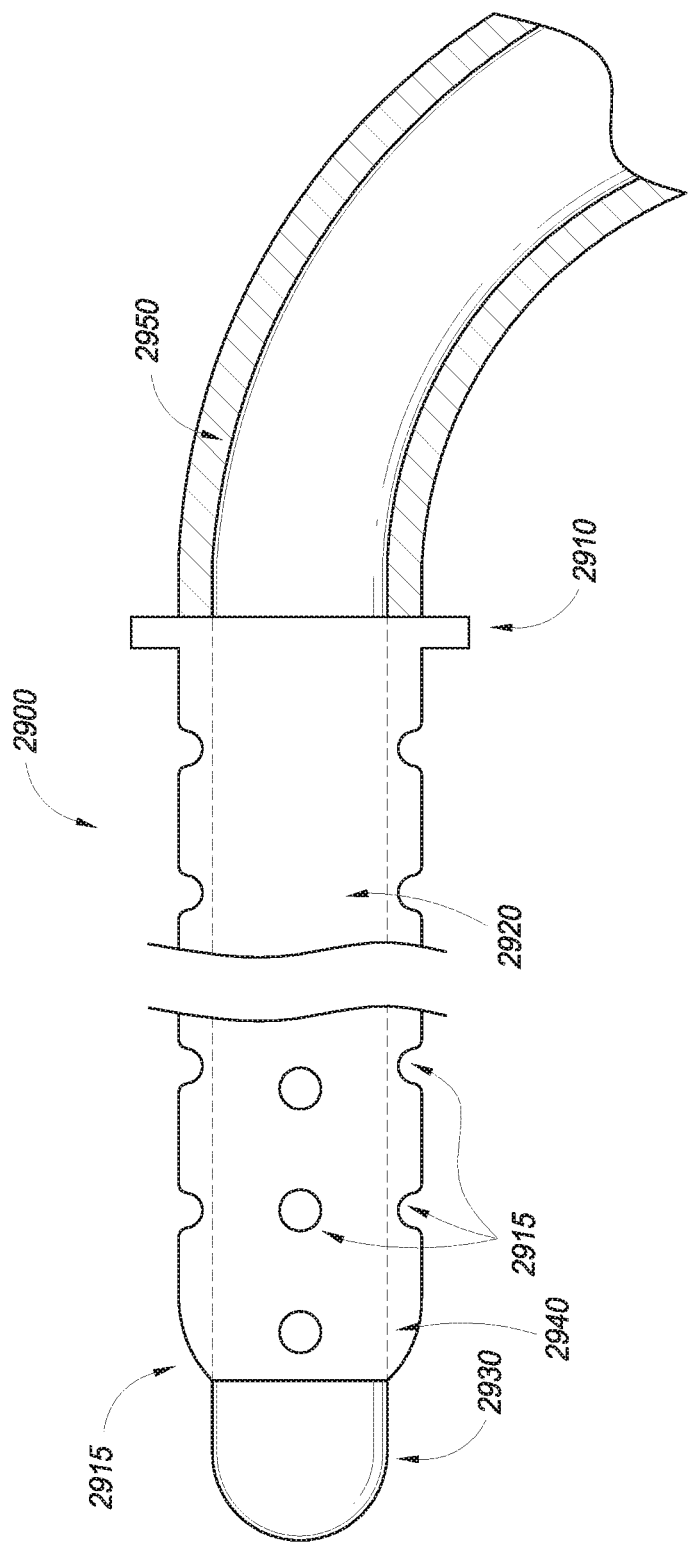
FIG. 19 illustrates a cross-sectional view of an embodiment of a delivery device and an associated sensor/shunt.

FIG. 19 shows another embodiment of a system that can be used to perform a variety of methods or procedures. In the illustrated embodiment, an over-the-wire system 2920 is used to deliver the sensor/shunt 2900. In some embodiments, both the sensor and the shunt are mounted on the wire. In other embodiments, while the sensor may be tethered or otherwise connected to the shunt, only the shunt portion is mounted on the wire. Such embodiments may be advantageous because the sensor portion may not need to have a passage through which the wire can be threaded, and this may simplify design of the sensor and layouts of electronic components. The sensor/shunt 2900 can have a generally rounded distal portion 2915 at the distal end. The radius of the distal portion can be about 70 to about 500 microns. The distal portion 2915 can gradually increase in cross-sectional size towards the proximal direction, preferably at a generally constant taper or radius or in a parabolic manner as shown.

In some embodiments, the implant comprises one or more openings 2905 communicating with an interior chamber, or lumen, within the implant. Preferably, the edges of the openings are rounded as shown. In addition or in the alternative, the implant can include other exterior surface irregularities (e.g., annular grooves) to anchor the implant, as described above.

In some embodiments the sensor/shunt can have a flange 2910 at a proximal portion of the implant. Preferably, the flange has sharp edges and corners as shown. The sharp edges and corners tend to inhibit cell proliferation near the influent end of the implant.

The wire or similar elongated structure 2920 can function as a trocar. Preferably, the wire 2920 is self-trephinating. The radius of the tip of the distal portion 2930 of the wire 2920 can be about 10 to about 500 microns. In some embodiments, the radius of the tip of the distal portion 2930 of the wire 2920 can be about 70 to about 200 microns. The distal portion 2930 of wire 2920 can increase in cross-sectional size towards the proximal direction. In some embodiments, the increase can be in a parabolic manner. In the depicted embodiment, the wire 2920 has a distal portion 2930 having a gradual increase in cross-sectional size in a parabolic manner towards the proximal direction. The wire 2920 can have a rounded distal tip of the distal portion 2930. In other embodiments, the distal portion can be tapered. The wire can be superelastic, flexible, or relatively inflexible with respect to the sensor/shunt. The wire can be pre-formed to have a certain shape. The wire can be curved. The wire can have shape memory, or be elastic. In some embodiments, the wire is a pull wire. The wire can be a steerable catheter.

In some embodiments, a pusher 2950 can be used in conjunction with the wire 2920 to aid in delivery of the sensor/shunt 2900. The pusher 2950 can be used to hold the sensor/shunt 2900 in place as the wire 2920 is withdrawn proximally after the sensor/shunt 2900 has been delivered to a desired location.

The pusher 2950, trocar 2920 and implant 2900 preferably are sized to fit and move (e.g., slide) within an outer sheath or needle. The needle preferably includes a sharpened distal end to penetrate tissue (e.g., corneal tissue) when accessing the anterior chamber of the eye.

Various embodiments of implantable physiological sensors, and associated methods, with a variety of features, have been described herein. Although not every embodiment has been illustrated with every feature, it should be understood that the features described herein can be freely combined with the various embodiments that are described and illustrated. The various physiological sensors described herein can also have any feature, characteristic, element, etc. that is disclosed in connection with the sensor devices described in the following U.S. patent documents, which are each hereby incorporated by reference in their entirety: U.S. Pat. No. 6,981,958; U.S. Pat. No. 7,678,065; U.S. Patent Publication 2010/0056979; and U.S. Patent Publication 2010/0106073. In addition, the various physiological sensors described herein can be used in, for example, any manner or application that is described in the foregoing patent documents.

The various illustrative logical blocks, modules, circuits, and algorithm steps described in connection with the embodiments disclosed herein can be implemented as, for example, electronic hardware (e.g., analog and/or digital circuitry), computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Some of the various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein.

Embodiments have been described in connection with the accompanying drawings. However, it should be understood that the figures are not necessarily drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure. The scope of certain inventions disclosed herein is indicated by the appended claims rather than by the foregoing description. All changes which come within the meaning and range of equivalency of the claims are to be embraced within their scope.

What is claimed is:

1. An intraocular glucose sensor comprising:
   an electrochemical glucose sensor configured to measure glucose concentration in aqueous humor of a patient's eye, the electrochemical glucose sensor having a fluid inlet port and a fluid channel enclosing a carrier member;
   a controller configured to take measurements of the glucose concentration in the aqueous humor using the electrochemical glucose sensor;
   a transmitter and an antenna, disposed on the carrier member and configured to wirelessly transmit the measurements to an external device;
   a glucose fuel cell for powering the controller and the transmitter, the glucose fuel cell enclosed within the fluid channel and configured to produce power using glucose in the aqueous humor within an anterior chamber of the patient's eye,
   wherein the electrochemical glucose sensor is in communication with the glucose fuel cell, such that the electrochemical glucose sensor measures glucose concentration in aqueous humor of the patient's eye based upon electrical current or voltage output of the glucose fuel cell; and
   a biocompatible housing, wherein the electrochemical glucose sensor, the controller, the transmitter, and the antenna are disposed within the biocompatible housing, the biocompatible housing being sized and shaped to be at least partially implanted in the supraciliary/suprachoroidal space of the patient's eye.

2. The glucose sensor of claim 1, wherein, when implanted, a first end of the biocompatible housing is configured to reside in the anterior chamber of the patient's eye and a second end of the biocompatible housing is configured to reside in the supraciliary/suprachoroidal space.

3. The glucose sensor of claim 1, further comprising a battery to power the controller and the transmitter.

4. The glucose sensor of claim 1, wherein the electrochemical glucose sensor is configured to measure the glucose concentration based on the amount of power produced by the glucose fuel cell.

5. The glucose sensor of claim 1, wherein the glucose fuel cell has a power output of at least about 10 µW.

6. The glucose sensor of claim 1, further comprising an electromechanical intraocular pressure sensor.

7. The glucose sensor of claim 1, wherein the controller is configured to take a measurement of the glucose concentration at least every hour.

8. The glucose sensor of claim 7, wherein the controller is configured to take a measurement of the glucose concentration at least every 15 minutes.

9. The glucose sensor of claim 8, wherein the controller is configured to take a measurement of the glucose concentration at least every minute.

10. The glucose sensor of claim 1, wherein the controller is further configured to perform data compression on the measurements.

11. The glucose sensor of claim 1, wherein the controller is further configured to cause the electrochemical glucose sensor or the transmitter to shut down or enter a power-saving state when the electrochemical glucose sensor is not in use.

12. The glucose sensor of claim 1, further comprising a temperature sensor for temperature correction of the electrochemical glucose sensor.

13. The glucose sensor of claim 1, further comprising a storage device that is configured to store the measurements.

14. The glucose sensor of claim 1, further comprising an anchor configured to attach the sensor in eye tissue.

15. The glucose sensor of claim 14, wherein the anchor is configured to extend into a physiological outflow pathway for the aqueous humor.

16. The glucose sensor of claim 15, wherein the anchor is configured to extend through the ciliary muscle attachment and into the uveoscleral pathway in the patient's eye.

17. The glucose sensor of claim 15, wherein the anchor is configured to extend through the trabecular meshwork and into Schlemm's canal in the patient's eye.

18. The glucose sensor of claim 15, wherein the sensor further comprises a fluid channel configured to permit the aqueous humor to flow from the anterior chamber through the fluid channel into the physiological outflow pathway.

19. The glucose sensor of claim 18, wherein the glucose fuel cell is in fluid communication with the fluid channel.

20. The glucose sensor of claim 1, further comprising an opening, configured for storage and controlled release of a drug.

21. A method of using the glucose sensor of claim 1, the method comprising inserting the glucose sensor into the patient's eye such that the electrochemical glucose sensor is provided in the anterior chamber of the eye.

22. A method of using the glucose sensor of claim 1, the method comprising:
    taking the measurements of glucose concentration in the aqueous humor; and
    transmitting the measurements to the external device.

23. The method of claim 22, wherein the external device is configured to communicate with an insulin pump, and wherein the method further comprises using the measurements to control the insulin pump.

24. The method of claim 22, wherein the external device comprises an insulin pump, and wherein the method further comprises using the measurements to control the insulin pump.

25. The method of claim 22, further comprising correlating the measurements of glucose concentration in the aqueous humor with blood glucose concentration.

26. A system comprising:
    an intraocular glucose sensor comprising,
    an electrochemical glucose sensor configured to measure glucose concentration in aqueous humor of a patient's eye, the electrochemical glucose sensor having a fluid inlet port and a fluid channel enclosing a carrier member;
    a controller configured to take measurements of the glucose concentration in the aqueous humor using the electrochemical glucose sensor, a transmitter and an antenna, disposed on the carrier member and configured to wirelessly transmit the measurements;

a glucose fuel cell for powering the controller and the transmitter, the glucose fuel cell enclosed within the fluid channel and configured to produce power using glucose in the aqueous humor within an anterior chamber of the patient's eye, wherein the electrochemical glucose sensor is in communication with the glucose fuel cell, such that the electrochemical glucose sensor measures glucose concentration in aqueous humor of the patient's eye based upon electrical current or voltage output of the glucose fuel cell;

a biocompatible housing, wherein the electrochemical glucose sensor, the controller, the transmitter, and the antenna are disposed within the biocompatible housing, the biocompatible housing being sized and shaped to be at least partially implanted in the supraciliary/suprachoroidal space of the patient's eye; and an external device configured to receive the measurements from the intraocular glucose sensor.

27. The system of claim 26, wherein the external device is configured to communicate with an insulin pump, and wherein the measurements are used to control the insulin pump.

28. The system of claim 26, wherein the external device comprises an insulin pump, and wherein the measurements are used to control the insulin pump.

* * * * *